US011400022B2

(12) United States Patent
Latorraca et al.

(10) Patent No.: US 11,400,022 B2
(45) Date of Patent: *Aug. 2, 2022

(54) MANAGING MEDICATIONS AT THE BEDSIDE

(71) Applicant: CareFusion 303, Inc., San Diego, CA (US)

(72) Inventors: Gary Latorraca, San Diego, CA (US); Kelly Larrabee, San Diego, CA (US); Thomas Utech, San Diego, CA (US); Jitendra Urankar, San Diego, CA (US); Guy Eldredge, San Diego, CA (US); Brendan Burgess, San Diego, CA (US); Maria Jaskela, San Diego, CA (US); David Heffron, San Diego, CA (US)

(73) Assignee: CAREFUSION 303, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/017,504

(22) Filed: Sep. 10, 2020

(65) Prior Publication Data
US 2020/0405577 A1 Dec. 31, 2020

Related U.S. Application Data

(63) Continuation of application No. 15/962,299, filed on Apr. 25, 2018, now Pat. No. 10,813,841, which is a (Continued)

(51) Int. Cl.
A61J 7/00 (2006.01)
A47B 96/00 (2006.01)
(Continued)

(52) U.S. Cl.
CPC ............ *A61J 7/0084* (2013.01); *A47B 81/00* (2013.01); *A47B 88/40* (2017.01); *A47B 96/00* (2013.01);
(Continued)

(58) Field of Classification Search
CPC ........ A61J 7/0084; A47B 81/00; A47B 88/40; A47B 96/00; E05B 65/46; G07C 9/00912;
(Continued)

(56) References Cited

U.S. PATENT DOCUMENTS 4,767,022 A 8/1988 Oldorf
4,785,969 A 11/1988 McLaughlin
(Continued)

FOREIGN PATENT DOCUMENTS

CA 2383290 C 7/2013
CN 1890672 A 1/2007
(Continued)

OTHER PUBLICATIONS

Japanese Office Action for Application No. 2020123732, dated Jun. 22, 2021, 5 pages including translation.
(Continued)

*Primary Examiner* — Michael Collins
(74) *Attorney, Agent, or Firm* — Morgan, Lewis & Bockius LLP

(57) ABSTRACT

Modular automated dispensing systems for dispensing secured medications in a medical environment are provided. The system includes a compact enclosure configured to be disposed in a medical treatment area without taking up valuable floor space. The system includes lockable drawers having one or more compartments for storing and dispensing medications or medical supplies. The system is unlocked by use of an access control interface internally or externally
(Continued)

connected directly to the system, or networked to the system through a medical center network.

20 Claims, 13 Drawing Sheets

Related U.S. Application Data continuation of application No. 14/959,514, filed on Dec. 4, 2015, now Pat. No. 9,962,316, which is a continuation-in-part of application No. 11/928,928, filed on Oct. 30, 2007, now Pat. No. 10,037,646.

(60) Provisional application No. 62/088,503, filed on Dec. 5, 2014.

(51) Int. Cl.
| | |
|---|---|
| *A47B 81/00* | (2006.01) |
| *E05B 65/46* | (2017.01) |
| *G07C 9/00* | (2020.01) |
| *G07F 11/62* | (2006.01) |
| *A47B 88/40* | (2017.01) |
| *G07F 9/02* | (2006.01) |
| *G07F 17/00* | (2006.01) |
| *G16H 10/40* | (2018.01) |
| *G16H 20/13* | (2018.01) |
| *G16H 10/60* | (2018.01) |
| *A61G 12/00* | (2006.01) |

(52) U.S. Cl.
CPC .......... *E05B 65/46* (2013.01); *G07C 9/00563* (2013.01); *G07C 9/00912* (2013.01); *G07C 9/00944* (2013.01); *G07F 9/026* (2013.01); *G07F 11/62* (2013.01); *G07F 17/0092* (2013.01); *G16H 10/40* (2018.01); *G16H 10/60* (2018.01); *G16H 20/13* (2018.01); *A61G 12/001* (2013.01)

(58) Field of Classification Search
CPC . G07C 9/00944; G07C 9/00563; G07F 11/62; G07F 17/0092; G07F 9/026; G06Q 50/24; A61G 12/001; G06F 19/3462; G16H 10/40; G16H 20/13; G16H 10/60
See application file for complete search history.

(56) References Cited

U.S. PATENT DOCUMENTS

| | | | |
|---|---|---|---|
| 5,036,462 A | 7/1991 | Kaufman et al. | |
| 5,842,976 A | 12/1998 | Williamson | |
| 5,957,372 A | 9/1999 | Dean et al. | |
| 5,961,036 A | 10/1999 | Michael | |
| 6,109,774 A | 8/2000 | Holmes | |
| 6,116,461 A * | 9/2000 | Broadfield | A61G 12/001 |
| | | | 206/443 |
| 6,175,779 B1 | 1/2001 | Barrett | |
| 6,338,007 B1 * | 1/2002 | Broadfield | A61G 12/001 |
| | | | 221/123 |
| 6,339,732 B1 * | 1/2002 | Phoon | A61J 7/0084 |
| | | | 700/237 |
| 6,502,718 B2 | 1/2003 | Fitzgerald et al. | |
| 6,775,591 B1 | 8/2004 | Shoenfeld | |
| 6,935,560 B2 | 8/2005 | Andreasson et al. | |
| 7,044,569 B1 | 5/2006 | Relyea | |
| 7,140,542 B2 | 11/2006 | Andreasson et al. | |
| 7,155,306 B2 | 12/2006 | Haitin et al. | |
| 7,175,081 B2 | 2/2007 | Andreasson et al. | |
| 7,182,256 B2 | 2/2007 | Andreasson et al. | |
| 7,232,066 B2 | 6/2007 | Andreasson et al. | |
| 7,258,249 B1 | 8/2007 | Frederick et al. | |
| 7,654,261 B1 | 2/2010 | Rockhold | |
| 7,668,620 B2 | 2/2010 | Shoenfeld | |
| 7,668,630 B2 | 2/2010 | Weber | |
| 7,689,316 B1 | 3/2010 | Frederick et al. | |
| 7,689,318 B2 | 3/2010 | Draper | |
| 7,693,603 B2 | 4/2010 | Higham | |
| 7,734,372 B2 | 6/2010 | Shoenfeld | |
| 7,885,725 B2 | 2/2011 | Dunn | |
| 8,111,159 B2 | 2/2012 | Andreasson et al. | |
| 8,326,455 B2 | 12/2012 | Dunn | |
| 8,473,097 B2 | 6/2013 | Shoenfeld | |
| 8,700,211 B2 | 4/2014 | Shoenfeld | |
| 8,744,621 B2 * | 6/2014 | Michael | A61B 50/18 |
| | | | 700/242 |
| 8,891,243 B2 | 11/2014 | Tanaka | |
| 9,962,316 B2 | 5/2018 | Latorraca | |
| 10,037,646 B2 * | 7/2018 | Heffron | G07F 17/0092 |
| 10,813,841 B2 * | 10/2020 | Latorraca | G07C 9/00563 |
| 2003/0109956 A1 | 6/2003 | Spano, Jr. et al. | |
| 2003/0120384 A1 | 6/2003 | Haitin et al. | |
| 2003/0160698 A1 | 8/2003 | Andreasson et al. | |
| 2003/0191670 A1 | 10/2003 | Hatcher et al. | |
| 2004/0010425 A1 | 1/2004 | Wilkes et al. | |
| 2005/0062238 A1 * | 3/2005 | Broadfield | G16H 40/20 |
| | | | 280/1 |
| 2005/0113969 A1 | 5/2005 | Spano, Jr. | |
| 2006/0032918 A1 | 2/2006 | Andreasson et al. | |
| 2006/0065726 A1 | 3/2006 | Andreasson et al. | |
| 2006/0136095 A1 | 6/2006 | Rob et al. | |
| 2006/0229551 A1 | 10/2006 | Martinez et al. | |
| 2006/0265102 A1 | 11/2006 | Bain | |
| 2007/0023513 A1 | 2/2007 | Andreasson et al. | |
| 2007/0043469 A1 | 2/2007 | Draper | |
| 2007/0088461 A1 | 4/2007 | Haitin et al. | |
| 2007/0093932 A1 | 4/2007 | Abdulhay et al. | |
| 2007/0156282 A1 | 7/2007 | Dunn | |
| 2007/0227204 A1 | 10/2007 | Shoenfeld | |
| 2007/0244598 A1 | 10/2007 | Shoenfeld | |
| 2009/0108011 A1 | 4/2009 | Heffron | |
| 2009/0114672 A1 | 5/2009 | Schifman | |
| 2010/0268378 A1 * | 10/2010 | Sharpley | A47J 31/52 |
| | | | 700/233 |
| 2011/0074543 A1 | 3/2011 | Kaczmarz et al. | |
| 2011/0125317 A1 | 5/2011 | Dunn | |
| 2012/0253510 A1 | 10/2012 | Thomas | |
| 2012/0274196 A1 * | 11/2012 | Arceta | B62B 3/1476 |
| | | | 312/249.11 |
| 2012/0310410 A1 * | 12/2012 | Adams | G07F 9/001 |
| | | | 700/237 |
| 2013/0079924 A1 | 3/2013 | Garda | |
| 2014/0145822 A1 | 5/2014 | Shoenfeld | |
| 2014/0163726 A1 * | 6/2014 | Shoenfeld | G07F 17/0092 |
| | | | 700/241 |
| 2014/0297027 A1 | 10/2014 | Tylenda | |
| 2015/0227127 A1 * | 8/2015 | Miller | G16H 20/13 |
| | | | 700/244 |

FOREIGN PATENT DOCUMENTS

| | | |
|---|---|---|
| CN | 101971220 A | 2/2011 |
| EP | 1075831 | 2/2001 |
| JP | 63212361 | 1/1988 |
| JP | 2002516228 A | 6/2002 |
| JP | 20042210486 | 7/2004 |
| JP | 2004528141 | 9/2004 |
| JP | 2006305099 | 11/2006 |
| JP | 2011502317 A | 1/2011 |
| JP | 2013501267 A | 1/2012 |
| RU | 2004133669 | 7/2005 |
| WO | WO-2002099231 | 12/2002 |
| WO | WO-2012142314 | 10/2012 |
| WO | WO-2013173015 | 11/2013 |

OTHER PUBLICATIONS

Australian Examination Report No. 3 in Australian Application No. 2008318610, dated Jul. 8, 2013, 3 pages.

(56) References Cited

OTHER PUBLICATIONS

Australian Examination Report No. 1 in Australian Application No. 2008318610, dated Jul. 19, 2012, 3 pages.
Australian Examination Report No. 2 in Australian Application No. 2008318610, dated Mar. 13, 2013, 3 pages.
Australian Notice of Acceptance in Australian Application No. 2008318610, dated Oct. 11, 2013, 1 page.
Australian Office Action for Application No. 2015357521, dated Jul. 9, 2019, 3 pages.
Brazil Office Action for Application No. PI0818833-5, dated Jun. 26, 2018, 5 pages.
Brazil Office Action for Application No. PI0818833-5, dated Mar. 25, 2019, 6 pages.
Brazilian Office Action for Application No. PI0818833-5, dated Nov. 16, 2018, 8 pages.
Canadian Office Action for Application No. 2703508, dated Aug. 20, 2015, 4 pages.
Canadian Office Action for Application No. 2703508, dated Jul. 19, 2016, 5 pages.
Canadian Office Action for Application No. 2703508, dated Jun. 13, 2017, 4 pages.
Canadian Office Action for Application No. 2703508, dated May 14, 2018, 5 pages.
Canadian Office Action in Canadian Application No. 2703508, dated Jul. 15, 2013, 2 pages.
Canadian Office Action in Canadian Application No. 2703508, dated Sep. 30, 2014, 3 pages.
Chinese Fifth Office Action for Application No. 200880113906.7, dated Aug. 9, 2016, 10 pages excluding English translation.
Chinese First Office Action Application No. 200880113906.7, dated Mar. 7, 2012, 11 pages.
Chinese Fourth Office Action for Application No. 200880113906.7, dated Mar. 18, 2016, 11 pages excluding translation.
Chinese Office Action for Application No. 200880113906.7, dated Feb. 7, 2017, 11 pages excluding translation.
Chinese Office Action for Application No. 201580074198.0, dated Jun. 1, 2020, 32 pages.
Chinese Office Action for Application No. 201580074198.0, dated Nov. 25, 2019, 28 pages.
Chinese Office Action for Application No. 201811241519.3, dated Jul. 24, 2020, 36 pages.
Chinese Second Office Action in Chinese Application No. 200880113906.7, dated Apr. 29, 2015, 22 pages.
Chinese Third Office Action for Application No. 200880113906.7, dated Nov. 4, 2015, 20 pages.
European Office Action for Application No. 08843739.7, dated Mar. 23, 2016, 6 pages.
European Office Action for Application No. 15813660.6, dated May 2, 2018, 9 pages.
European Office Action for Application No. 19184418.2, dated Aug. 24, 2020, 6 pages.
Extended European Search Report for Application No. 19184418.2, dated Aug. 16, 2019, 8 pages.
India Office Action for Application No. 1437/KOLNP/2010, dated Aug. 16, 2018, 6 pages.
International Preliminary Report on Patentability for Application No. PCT/US2008/081802, dated May 4, 2010, 6 pages.
International Search Report and Written Opinion for Application No. PCT/US2015/064105, dated Feb. 9, 2016, 11 pages.
International Search Report for Application No. PCT/US2008/081802, dated Aug. 26, 2009, 2 pages.
Japanese Office Action dated Dec. 18, 2012, 3 pages.
Japanese Office Action for Application No. 2017-529658, dated Mar. 13, 2020, 5 pages.
Japanese Office Action for Application No. 2017-529658, dated Oct. 29, 2019, 11 pages.
New Zealand Office Action in New Zealand Application No. 584756, dated Jul. 12, 2011, 2 pages.
Notification of the Decision of Rejection in Chinese Application No. 200880113906.7, dated Oct. 15, 2011, 17 pages.
Russian Decision of Grant in Russian Application No. 2010121904, dated Dec. 6, 2013.
Russian Office Action in Russian Application No. 2010121904, dated Jul. 15, 2013, 11 pages.
Russian Office Action in Russian Application No. 2010121904, dated Nov. 23, 2012, 14 pages.
Summons to attend oral proceedings for European Application No. 08843739.7, dated Jul. 2, 2018, 7 pages.
Chinese Office Action for Application No. 201811241519.3, dated Feb. 26, 2021, 8 pages including translation.
European Office Action for Application No. 19184418.2, dated Apr. 22, 2021, 8 pages.
Chinese Office Action for Application No. 201580074198.0, dated Oct. 27, 2020, 15 pages including machine translation.
Canadian Office Action for Application No. 2969461, dated Jan. 31, 2022, 4 pages.
Japanese Office Action dated Feb. 15, 2022, 4 pages including translation.

* cited by examiner

MANAGING MEDICATIONS AT THE BEDSIDE

CROSS-REFERENCES TO RELATED APPLICATIONS

This application is a continuation application of U.S. application Ser. No. 15/962,299 filed on Apr. 25, 2018, entitled "MANAGING MEDICATIONS AT THE BEDSIDE," which issued on Oct. 27, 2020, as U.S. Pat. No. 10,813,841, which is a continuation application of U.S. application Ser. No. 14/959,514 filed on Dec. 4, 2015, entitled, "MANAGING MEDICATIONS AT THE BEDSIDE," which issued on May 8, 2018, as U.S. Pat. No. 9,962,316, which is a continuation-in-part application of U.S. application Ser. No. 11/928,928 filed on Oct. 30, 2007, entitled "MANAGING MEDICATIONS AT THE BEDSIDE," which issued on Jul. 31, 2018, as U.S. Pat. No. 10,037,646, and which claims the benefit of U.S. Provisional Application No. 62/088,503 filed Dec. 5, 2014, all of which are herein incorporated by reference in their entireties.

BACKGROUND

Everyday, patients hospitalized because of age, infirmities, or accidents, receive unsatisfactory care. Dissatisfaction can arise when a request for medication is responded to in an untimely manner. In some instances, hours can pass without response to a patient's requests. Often, the untimely response results from the overburdening of caregivers that occurs due to the numerous tasks associated with the daily care of hospitalized individuals, including dispensing and administrating medications.

Caregivers use a centralized inventory system for dispensing and administering medications. In this system, medications are stored in a centralized area. Both required and optional medications are dispensed and administered to each patient by retrieving medications from a centralized inventory onto a movable cart. In some instances, a caregiver follows a prescribed schedule for administering required medication to a patient and provides optional medication upon request by the patient. Optional medication often includes pro re nata (PRN) medication. PRN medication refers to dosages of prescribed medication that are not scheduled, and administration is left to the caregiver or the patient's prerogative. PRN is often added to the prescribed directions for medication used to treat symptoms (e.g., pain/fever, constipation, insomnia, anxiety, nausea/vomiting). Most often PRN medications are analgesics, such as paracetamol (Tylenol) or hydrocodone (Vicodin), laxatives, such as coloxyl, sleeping aids (sedatives), such as zolpidem (Ambien) or lorazepam (Ativan), and antiemetics, such as ondansetron or dimenhydrinate (Gravol). These medications can include over-the-counter drugs that would be readily available to the patient but for the patient's admittance into the hospital or care facility.

Upon request by the patient to receive the optional medication, the caregiver retrieves the medication from the centralized inventory and returns to the patient to administer the optional medication. The patient often requests the optional medication during administration of the required medication, at which time, caregivers proceed to each patient's room dispensing and administering the required medications. When optional medication, such as PRN medication, is requested, the caregiver exits the patient's room and retrieves the optional medication from the centralized inventory and returns to the patient's room to administer the medication. After administration of the optional medication, the caregiver proceeds to the next patient to administer the required medication, and this patient may also request optional medication. Accordingly, the caregiver again returns to the centralized inventory to retrieve the requested optional medication and returns to the patient for administration.

SUMMARY

Some aspects of the present disclosure provide a modular automated dispensing system for dispensing secured medications in a medical environment. The modular automated dispensing system includes a compact enclosure configured to be disposed on a support surface in a medical treatment area. The compact enclosure includes a front surface and a top surface, a drawer lock assembly, a drawer for storing medications, the drawer configured to be secured in the compact enclosure when locked by the drawer lock assembly and slideably openable from the front surface of the compact enclosure when unlocked by the drawer lock assembly, a plurality of compartments disposed within the drawer, and a biometric device built into the top surface of the compact enclosure, the biometric device operatively coupled to a processor and to the drawer lock assembly, the biometric device configured to provide a first signal to the processor, the first signal comprising one of a registration signal, a login signal and an authentication signal, and to provide a second signal to the drawer lock assembly, the second signal comprising an unlock signal to unlock the drawer, the second signal based on received authorization input from the processor, wherein the drawer is fully openable to expose all of the plurality of compartments when unlocked by the second signal.

Some aspects of the present disclosure provide a system for dispensing secured medications in a medical environment. The system includes a plurality of modular automated dispensing devices. Each modular dispensing device includes a compact enclosure configured to be disposed on a support surface above a floor in a medical treatment area. The compact enclosure includes side surfaces, a rear surface, a front surface, a bottom surface and a top surface, a drawer lock assembly, a drawer for storing medications, the drawer configured to be secured in the compact enclosure when locked by the drawer lock assembly and slideably openable from the front surface of the compact enclosure when unlocked by the drawer lock assembly, a plurality of compartments disposed within the drawer, and a biometric device recessed within the top surface of the compact enclosure, the biometric device operatively coupled to a processor and to the drawer lock assembly, the biometric device configured to provide a first signal to the processor, the first signal comprising one of a registration signal, a login signal and an authentication signal, and to provide a second signal to the drawer lock assembly, the second signal comprising an unlock signal to unlock the drawer, the second signal based on received authorization input from the processor, wherein the drawer is fully openable to expose all of the plurality of compartments when unlocked by the unlock signal.

The present disclosure provides methods and systems for dispensing medication. The methods and systems dispense medications from a fixed dispensing apparatus located in, or in close proximity to, an individual patient's room. A movable dispensing apparatus may dispense other medications. The fixed dispensing apparatus may dispense optional medications and/or required medications, providing increased satisfaction of a hospitalized patient by decreasing a delay time for receiving requested medications. These methods and systems reduce the number of times that a caregiver is required to return to a central storage location to retrieve medication for a patient. Moreover, these methods and systems provide an efficient manner for a caregiver to administer medications to a patient while maintaining control over the medications by the care facility.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure. In the drawings.

DETAILED DESCRIPTION

Figure 1A:
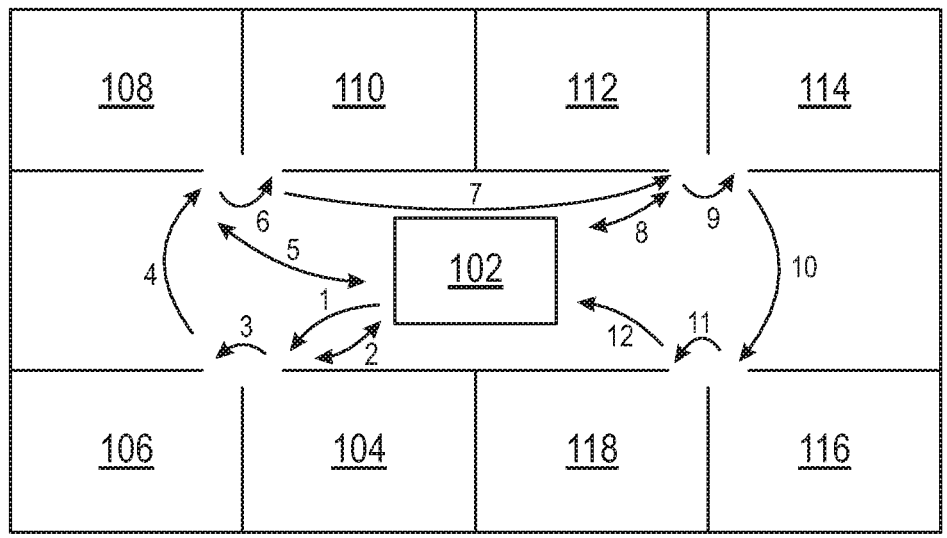
FIG. 1A is a diagram of a hospital that indicates a path taken by a caregiver to dispense medications to patients.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

Within this document, the phrases "portable user interface device" and "PUID" mean any mobile device that provides information and accepts input. A PUID may provide information via any channel including but not limited to an optical display such as a light-emitting diode (LED) screen and an audible actuator such as a speaker or buzzer. A PUID may accept input via any channel including but not limited to an optical scanner, a radio-frequency identification (RFID) reader including electric-field and magnetic-field systems, a keyboard, a touchscreen or stylus-activated screen, a microphone, and a joystick. PUIDs may include but are not limited to tablet computers, laptop computers, desktop computers installed on a mobile platform, personal data assistants (PDAs), cellular phones, wirelessly connected devices such as iPods and iPads, and readers such as Kindle e-readers.

Within this document, the term "medication" comprises substances that are conventionally considered to be medications, particularly substances that are available only by a doctor's prescription, as well as any other substance or mixture that may be used in a health-related treatment of a patient. Medications include but are not limited to medical fluids such as a saline solution or Ringer's lactate, active compounds such as an analgesic and an antimicrobial, and health-related substances such as a vitamin.

Within this document, the term "scanning" means the input of a machine-readable feature and interpretation of the information encoded therein. Scanning may include passive optical observation and recording of a visual image, such as a barcode or 2D coded matrix, or may include active illumination, such as provision of a light beam that traverses a portion of the image, as is commonly done in a barcode scanner. Scanning may also include provision of an energizing field, such as an electric field or magnetic field as are commonly provided to read passive RFID tags.

Within this document, the term "portable" means a size and weight that is easily moved by an adult. While an object of any size and weight can be moved, with the use of appropriate equipment, a portable device as considered herein would include devices of a size and weight that they would not be burdensome to a person to keep with them for several hours over the course of an 8-hour workday. Portable devices may be mounted on a rolling cart or other movable appliance, such as the wheeled computer platforms commonly used in hospitals and known to those of skill in the art. Portable devices are generally not secured to a single location for extended periods of time during which the devices are used.

It is known in the medical community, and in particular, in acute care facilities like hospitals, to use a centralized inventory system for dispensing and administering medical items (or "line items"). Many facilities today utilize centralized automated dispensing cabinets ("automated dispensing machines," "ADM," or "dispensing unit") to store medical items and provide drug distribution to patient care areas, an example of which is shown in FIG. 1. Each ADM includes one or many storage spaces for the storing of items.

These centralized automated dispensing cabinets provide a wide range of medical items that meet the patient care needs for the patient care area. It is common for as high as 95% of the medication items for patients in a specific care area to be fulfilled by a centralized automated dispensing cabinet. Accordingly, a typical ADM has a large footprint that requires significant floor space in a hospital or other medical environment.

In some aspects, the present disclosure generally relates to medications. More specifically, the present disclosure relates to dispensing medications from separately placed apparatuses to increase the efficiency of caregivers and the overall satisfaction of patients. In accordance with the present disclosure, an individualized dispensing apparatus located near each individual patient carries optional medications. A separate dispensing apparatus carries required medications and is capable of servicing multiple patients. By using more than one apparatus to dispense medications, caregivers do not have to retrieve optional medications at a central storage location each time a request has been made for the optional medications. Neither does the caregiver have to return to stock unused medications.

Two types of medications are typically given to patients, required and optional. Medications which treat the condition of the patient are called required medications and are patient specific. Often, these medications are associated with a prescription that is issued by a medical professional. Required medications are generally more expensive than optional medications.

Optional medications are generally used to relieve pain and discomfort. These can include PRN medications. PRN medications, as used herein, is intended to have its plain and ordinary meaning, which includes, without limitation, medications that are made available for a patient if needed, but which are not part of a daily prescribed regimen. There is generally no requirement on the times and doses used for optional medications, but the amount used may be limited by the specific manufacturer of the optional medication. Optional medications are characterized as being relatively inexpensive.

Figure 1B:
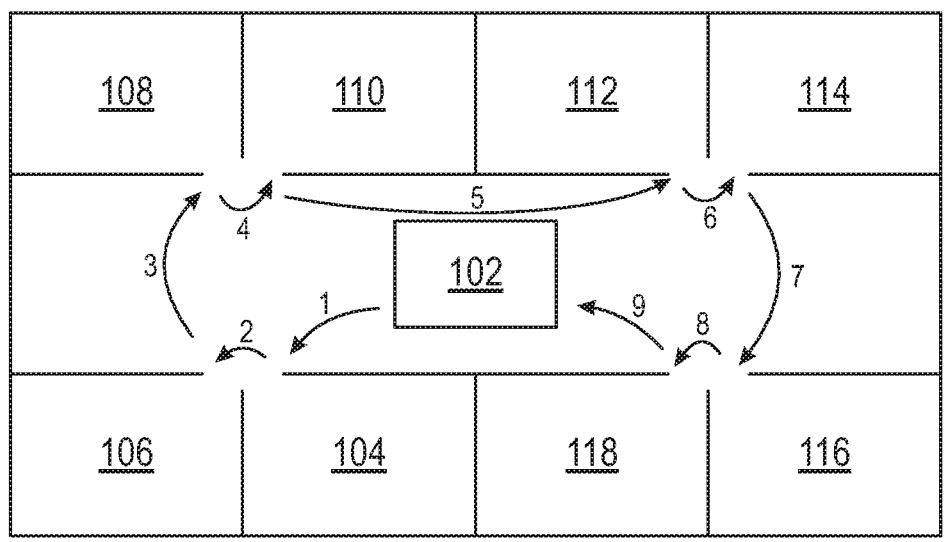
FIG. 1B is a diagram of a hospital that indicates another path taken by a caregiver to dispense medications to patients.

Now referring to FIGS. 1A and 1B, diagrams 100 indicating paths taken by caregivers to dispense medications to patients are presented. In the middle of the diagrams 100, a central storage location 102 is shown. Required and optional medications are kept at the central storage location 102. Preparation of required medications are made at the central storage location 102 to distribute them to the individual patients by the caregivers. The medications are placed on trays for each patient and placed onto a movable medical cart or medical station. As used herein, the term cart is a broad term, is used in its ordinary sense, and is intended to include, without limitation, a decentralize storage system or apparatus, which can be, for example, a MEDSTATION® provided by CareFusion 303, Inc. By utilizing the movable cart, caregivers can administer the individualized required medications for each hospitalized patient without returning to the central storage location 102 for each patient's required medication needs.

To maintain the appropriate amount of required and optional medications, the central storage location 102 tracks information regarding the amount of medications left and whether more medications need to be ordered. In certain embodiments, the information tracked by the central storage location 102 is received directly from the caregivers. Alternatively, the information is received from dispensing apparatuses. Each dispensing apparatus sends administrative information to an electronic inventory management device used at the central storage location 102. The electronic inventory management device then processes the administrative information.

Continuing with FIGS. 1A and 1B, a plurality of patients' rooms 104-118 are shown. Each patient's room is spaced apart from one another. One skilled in the art would understand that a room can include physical barriers such as walls and doors. Alternatively, the rooms can be partitioned by screening devices such as cloth dividers. Although eight rooms 104-118 are shown, the hospital can include more or less rooms dependent on the size and constraints of the hospital.

With reference now to FIG. 1A, a caregiver's route using a single dispensing apparatus for each individual's required medicinal needs is presented. The route begins when the caregiver proceeds to room 104 to administer required medications to the patient therein. During the administering of the required medication, the patient requests an optional medication for his/her headache or similar type of infirmity. Because the cart does not contain the optional medication, the caregiver is required to return to the central storage location 102 and retrieve it. This not only requires an additional trip by the caregiver, but wastes valuable time for the caregiver to attend to other medical needs of the patient.

Continuing, the next stop for the caregiver is room 106. The patient in room 106 does not request any optional medications and after administering the required medications to the patient, the caregiver proceeds to the next patient in room 108. This time, however, the patient in room 108 requests an optional medication for a sleeping aid or similar type of medication. Again, the caregiver would have to return to the central storage location 102 and retrieve the appropriate optional medication.

The caregiver then proceeds to rooms 110 and 112. At room 112, the caregiver for the third time returns to the central storage 102 and retrieves a user-requested optional medication. The caregiver then services the patients of rooms 114, 116, and 118. Each time the caregiver returns to the central storage location 102 for optional medications, the caregiver wastes valuable time that could have been used to take care of the patients.

Alternative implementations exist to servicing patients with optional medication requests. Accordingly, the caregiver could administer the required medications of the patients in rooms 104-118 first and then afterwards, administer optional medications that were requested while the caregiver was in the patient's room 104-118. The caregiver would still have to visit the central storage location 102 to retrieve the optional medications. The caregiver would also be required to write down or memorize each patient's optional medicinal needs. Still further, there may be considerable delay time when a first patient requests the optional medication and the response to that request by the caregiver.

In yet further embodiments, a request for optional medication can occur when the caregiver is in another patient's room 104-118. In response, the caregiver would retrieve the requested optional medications at the central storage location 102. The caregiver would then proceed to the requesting patient's room to dispense and administer the optional medication. The caregiver would then return to the room the caregiver was at before receiving the request.

In some embodiments, the optional medications may be stored on the medical cart. The optional medication, however, would have to be returned to the central storage location 102 when the caregiver has completed his/her routes. Consequently, the medication would be handled numerous times. For example, each time the medication is used, the medication would be loaded onto the cart and then unloaded at the central storage location 102 when the caregiver has completed his/her routes. Filling and restocking the medication would decrease the amount of time that the caregiver has for the other needs of the patients.

With reference now to FIG. 1B, a caregiver's route using multiple dispensing apparatuses for each individual's medicinal needs is presented. In addition to the apparatus used for dispensing required medications to each individual patient, another apparatus for dispensing optional medications within each individual patient's room 104-118 is used. Because each room 104-118 can individually dispense optional medications, each room 104-118 can be serviced without the caregiver returning to the central storage location 102. The caregiver can proceed to room 104, room 106, and so on without wasting valuable time. Thus, a caregiver can tend to the patient's other needs.

Figure 2:
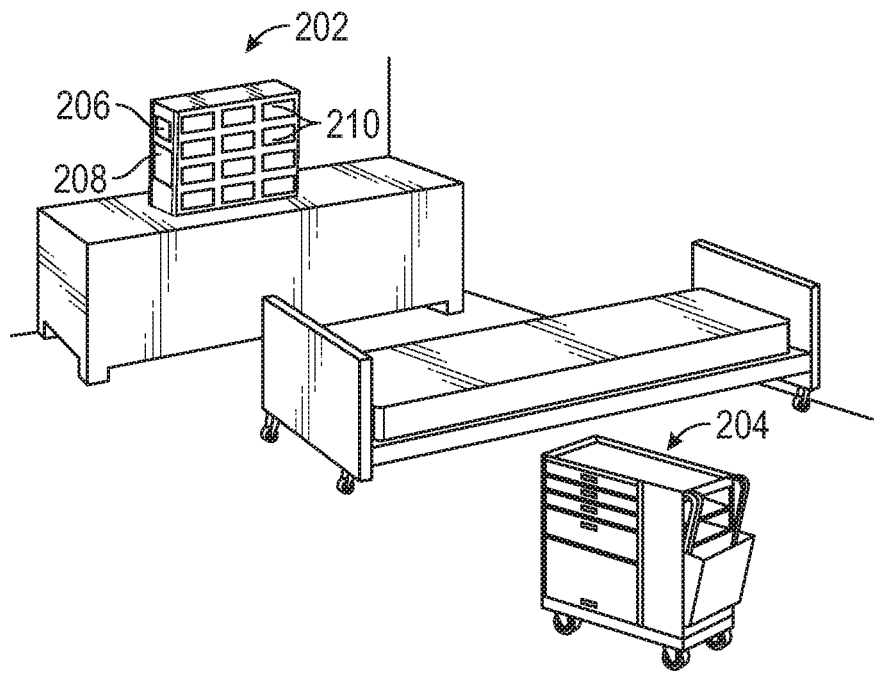
FIG. 2 is a block diagram of an individual patient's room along with a first and second apparatus for dispensing medications in accordance with embodiments of the present disclosure.

Now referencing FIG. 2, an apparatus for dispensing optional medications 202 located in, or in close proximity to, each room 104-118 in conjunction with a medical cart 204 movable to multiple rooms 104-118 is presented. Apparatus 202 can contain numerous compartments where each compartment can contain a different type of optional medication such as Tylenol, sleeping medications, etc. Combined with the medical cart 204, both required and optional medication administrations can be performed without leaving the room 104-118.

The dispensing apparatus 202 can contain a locking device 206 to limit access of the optional medications to the individual patients within the rooms 104-118. Such locking devices 206 would prevent drawers 210 of the dispensing apparatus 202 from being opened. One locking device 206 can be a lock and key device. Alternatively, the locking device 206 can be a fingerprint recognition device. Further, the locking device 206 can be a voice recognition system or a combination lock. One of ordinary skill in the art would recognize that there are many types of locking devices 206 that can prevent the apparatus 202 from being opened, or, in other words, there are many types of locking devices 206 that can restrict access to the optional medications in the dispensing apparatus 202 and that can provide access to the optional medications by only those authorized to retrieve the medications. In still yet other embodiments, the apparatus 202 does not need a locking device 206.

The dispensing apparatus 202 can also include a user interface 208 for the caregiver, or other authorized personnel, to provide instructions to the apparatus 202 relating to the requested optional medication. For instance, in some embodiments, the caregiver approaches the dispensing apparatus 202 and gains access to the user interface 208 by passing a security check provided by the locking device 206, which can be, for example, a fingerprint recognition device. Upon gaining access to the user interface 208 and having cleared the security check, the caregiver can specify which optional medication is requested. Upon receiving the request, the apparatus 202 can open one of the drawers and allow the caregiver to retrieve and administer the medication. In some embodiments, the user interface 208 is an LCD screen that displays the contents of the apparatus 202 and that provides input means, for example, a keyboard, buttons, or touch-screen, for the caregiver to provide input to the apparatus 202.

In further embodiments, the caregiver may specify the requested medication prior to passing the security check. This may be advantageous if various optional medications have differing degrees of security checks or if limitations are placed on particular medications due to potential conflicts with other required medications. To access the medication, the caregiver would approach the apparatus 202 and identify via the user interface 208 the requested medication. In some embodiments, the apparatus 202 confirms whether the medication is compatible with the medications currently being administered to the patient, and upon clearance, the apparatus 202 can request the caregiver to unlock or otherwise deactivate the locking device 206. Upon confirming that the caregiver is authorized to gain access to the optional medication, the apparatus 202 can then unlock the specific drawer 210 corresponding to the medication, open the drawer 210 containing the medication, or otherwise dispense the medication for the caregiver to administer.

In the embodiments shown in FIG. 2, the optional medicine dispensing apparatus 202 is affixed to the room. In some embodiments, the apparatus 202 can be affixed to the patient's bed. The apparatus 202 can also be affixed to a table near the patient. One of ordinary skill in the art would appreciate that the apparatus 202 can be attached to any item which is fixed. In some embodiments, the apparatus 202 may be movable within the patient's room 104-118. In yet other embodiments, the apparatus 202 is positioned in close proximity to the patient's room. For example, in some embodiments, the apparatus 202 is affixed to a wall outside the patient's room.

In some embodiments, the apparatus 202 can be actuable from a central location. For example, with reference to FIG. 4, the apparatus 202 can be configured to be operable by the caregiver at a terminal, or central control 212, located at the caregiver's station. When a patient desires to receive an optional medication, the patient can call the caregiver and make the request. Some embodiments provide that the caregiver is able to remotely open the apparatus 202 from the caregiver's station through the central control 212. This is particularly beneficial with ambulatory patients that are capable of getting out of bed and retrieving the medications without assistance. The central control 212 can be a terminal that is directly, wirelessly, or otherwise connected to one or more dispensing apparatus 202.

Figure 4:
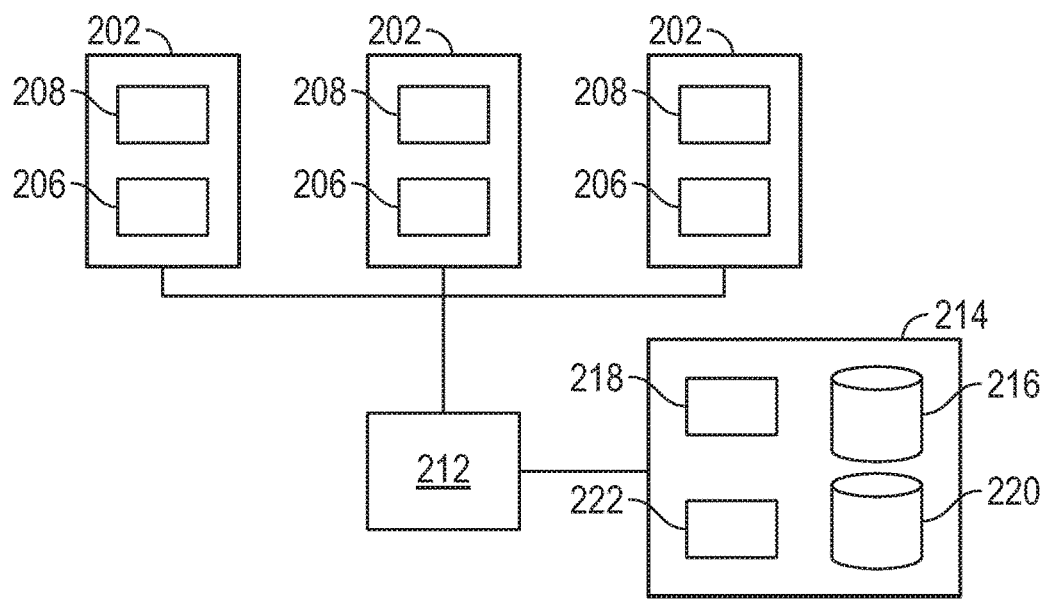
FIG. 4 depicts a schematic view of embodiments of a dispensing apparatus as discussed herein.
Figure 5:
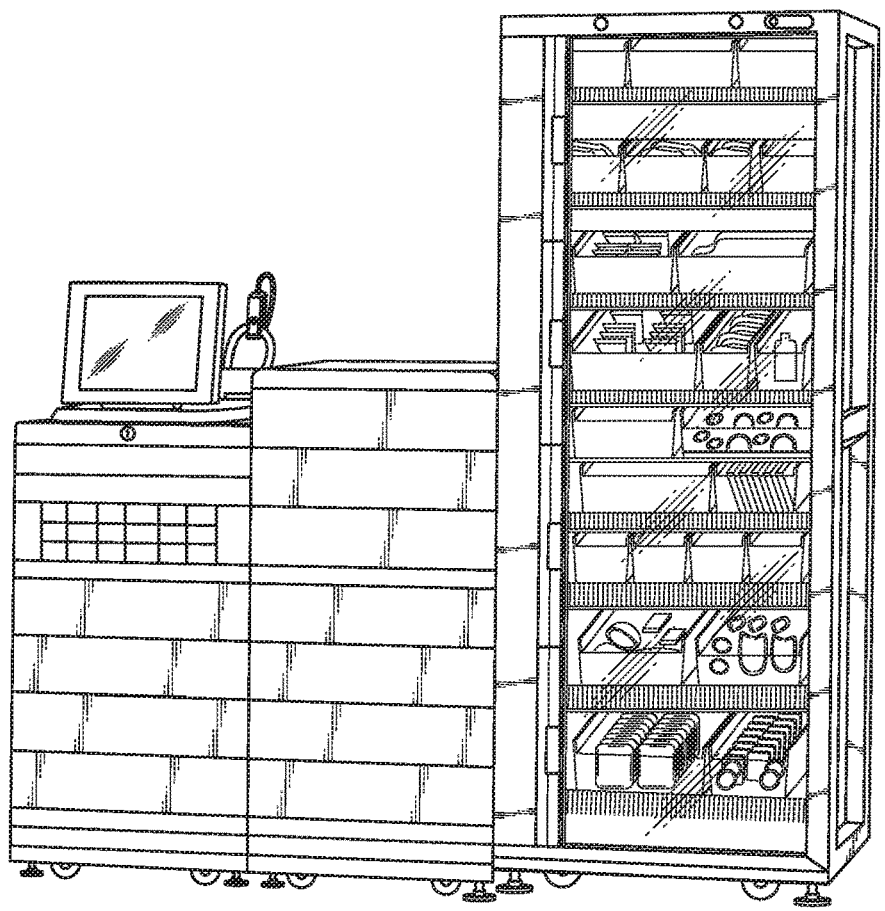
FIG. 5 is a front perspective view of one or more embodiments of an automated dispensing machine.

The central control 212 can also be similarly connected to other electronic modules at the care facility. For example, in some embodiments, as depicted in FIG. 4, the central control 212 is directly, wirelessly, or otherwise connected to a care facility management module 214. The care facility management module 214 can include an accounts receivable database 216 and accounts receivable processor 218 that keeps track of and processes all expenses for which a particular patient will be billed. In some embodiments, information from the administration of optional medication is automatically transmitted from the dispensing apparatus 202 to the accounts receivable database 216 through the central control 212 and accounts receivable processor 218. This information can be processed and automatically added to the patient's bill.

The care facility management module 214 can also include a personnel information database 220 and personnel information processor 222. The personnel information database 220 can include, among other things, information relating to accessing the dispensing apparatus 202 by care facility personnel. For example, the personnel database 220 can include a caregiver's fingerprint for verification when the caregiver attempts to obtain access to an apparatus 202 through a fingerprint reader. When the caregiver's fingerprint is read by the locking device 206 of the apparatus 202, the personnel information processor 222 or the central control 212 can access the personnel database to determine whether the caregiver is authorized to access the requested medication. Accordingly, a caregiver that is asked to care for patients in new rooms that the caregiver is not normally assigned is still able to gain access to the dispensing apparatus 202 in those new rooms because the caregiver's personnel information is stored at a centralized location that can be accessible to all dispensing apparatuses 202 in the care facility. Moreover, the administration of medications by a particular caregiver can also be monitored by retrieving from the personnel database the day and time that the caregiver sought access to any one or all dispensing apparatus 202 in the facility.

In some embodiments, records relating to how many medications remain within the apparatus 202 are preferably kept at the central control 212. Accordingly when any one medication needs to be replenished, a indicator may be provided on the apparatus or at the central control 212. In some embodiments, the indicator provides the name and quantity of optional medication that needs to be replaced.

Additionally, when the caregiver provides remote access to the apparatus 202, such as through the central control 212, the apparatus 202 preferably only provides access to a single dose of the requested optional medication. In some embodiments, the medications are contained within a drawer 210, and the drawer 210 is divided into compartments that are configured to only provide a single-dose of the medication. When the caregiver opens the drawer for the patient or a caregiver, whether remotely or otherwise, the drawer preferably only opens to the point that it provides the next dosage of medication. Accordingly, the apparatus 202 can monitor, or keep track of, what medications are stored within and dispensed from the apparatus 202.

Figure 3:
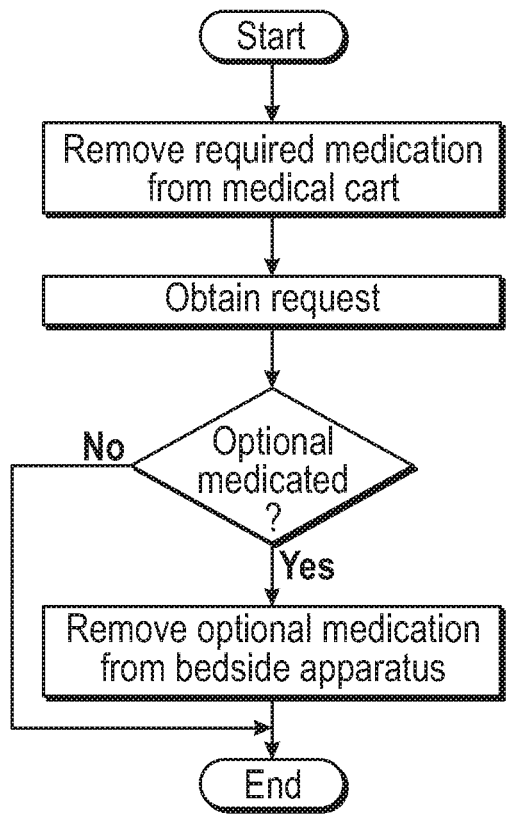
FIG. 3 is a flow diagram for dispensing medication corresponding to a patient's request in accordance with embodiments of the present disclosure.

Now referring to FIG. 3, a flow diagram 300 for using two dispensing apparatuses to timely satisfy a patient's request is presented. Beginning at block 302, the caregiver begins to administer the required medication from the medical cart 204 to the patient of the room 104-118. While the caregiver is in the room 104-118, the caregiver obtains a request made by the patient at block 304.

At determination block 306, the caregiver determines whether the request was for an optional medication. The caregiver removes the optional medication from the apparatus 202 and administers the optional medication to the patient at block 308 when there was a request for the optional medication. In some embodiments, the caregiver is required to unlock a device associated with the apparatus 202. The caregiver can use their key to open a lock. Alternatively, the caregiver can use their fingerprint signature to open the lock. Also, the caregiver can use their voice to open the lock. These are exemplary only, as other methods for authentication may be employed to control the unlocking of the device. Thereafter, the caregiver proceeds to the next room ending the patient's care at block 310.

In further embodiments of the present disclosure, the caregiver, who is located in another patient's room 104-118, receives a request from a patient in another room 104-118. To satisfy the request, the caregiver enters to the requesting patient's room 104-118 and removes the optional medicine from the dispensing apparatus 202 associated with the individual patient. By using the apparatus 202, valuable time is saved by not having to retrieve the optional medicine from the central storage station 102. Thereafter, the caregiver returns to the other patient's room 104-118.

In order to facilitate management of pharmaceutical needs, administrative information is logged each time the optional medication dispensing apparatus 202 is used. Either the caregiver can directly log the information or the apparatus 202 provides an automatic logging function. The apparatus 202 provides the information to an electronic inventory management device at the central storage location 102. In this way, the central storage location 102 can manage both the number of optional and required medications left and can make appropriate pharmaceutical requests.

In some embodiments, when the patient requests and receives optional medication, access to the apparatus 202 triggers an electronic signal that is processed by a processing unit to indicate with what medication the patient was treated. This can be used to keep records on medication intake as well as for billing purposes. For example, in some embodiments, when the patient requests optional medication, the apparatus 202 sends notification of the treatment to the patient's records for inclusion in billing the patient for the provided medications. Accordingly, the apparatus 202 provides automatic billing accountability for administering optional medications.

Through the use of the optional medication dispensing apparatus 202, fewer medications will be returned to the central storage location 102. Accordingly, the optional required medication can be left in the room 104-118 with the individual patients. By not refilling and restocking the optional medications, the medications are handled fewer times and increase the amount of time that a caregiver has to tend to other needs of the patients. Additionally, tighter controls are kept on the medication to reduce loss through, for example, staff use.

The optional medication dispensing apparatus 202 further permits the optional medication inventory to be adjusted by the caregiver, who is likely familiar with the needs of the individual patient and has access to bulk quantities of medications at the central storage location 102. As demand for certain medications changes, the caregivers can add or remove medications that are stored in the rooms. Moreover, by knowing what ailments the patient is suffering, or will likely suffer, the caregiver can provide specific medications in the dispensing apparatus 202 to ensure that such medications are not exhausted during the patient's time in the hospital or care facility. Additionally, if optional medications may have adverse effects when combined with the patient's required medication, the caregiver can selectively replace the optional medication in the dispensing apparatus 202 with medication that is more compatible with the required medication.

With the optional medication located in the dispensing apparatus 202, the caregiver is able to respond immediately to the patient's request and administer the medication. This quick response to the patient's request will increase patient satisfaction and can reduce stress and distress that may otherwise be experienced by a patient who has to wait long periods of time for a caregiver to retrieve optional medication. Additionally, the optional medication in the dispensing apparatus 202 reduces mistakes that may otherwise occur when the caregiver returns to the central storage location 102.

In some aspects, the subject technology provides for a modular automated dispensing machine ("MADM") having a form factor suitable for a wide variety of environments requiring secure storage and dispensing of medications. For example, MADMs may be used to securely store and dispense medications in typical acute care facilities (e.g., nursing floor, central pharmacy, procedural areas, outpatient), either in place of or in conjunction with a typical ADM. Many other areas that would not support the use of a typical ADM may be served with the use of one or more MADMs. For example, MADMs may be used in medical clinics/centers (e.g., ambulatory clinic, urgent care center, oncology clinic, surgery center, dialysis clinic, non-acute care procedural areas), long term care/post-acute areas (e.g., hospice, assisted living, home health, nursing home, adult day services, outpatient rehab, inpatient rehab), pharmacy services (e.g., mail order, research lab, nuclear, retail, compounder, specialty, medication re-packager), and manufacturing/distribution (e.g., pharmaceuticals, disposables, medical devices).

Figure 6:
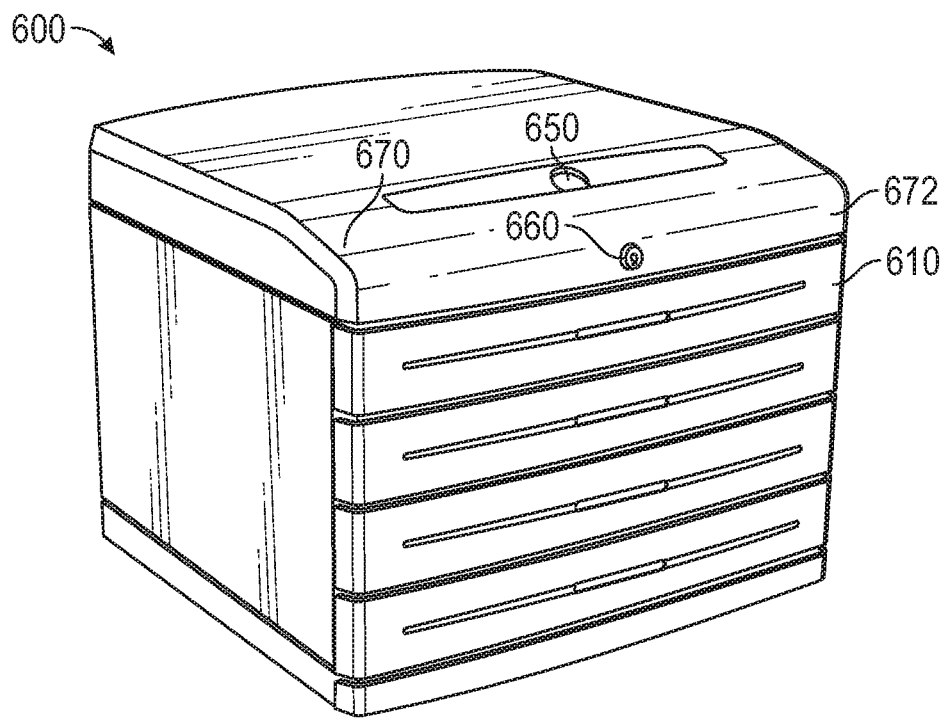
FIG. 6 is a perspective view of one or more embodiments of a modular automated dispensing machine.
Figure 7:
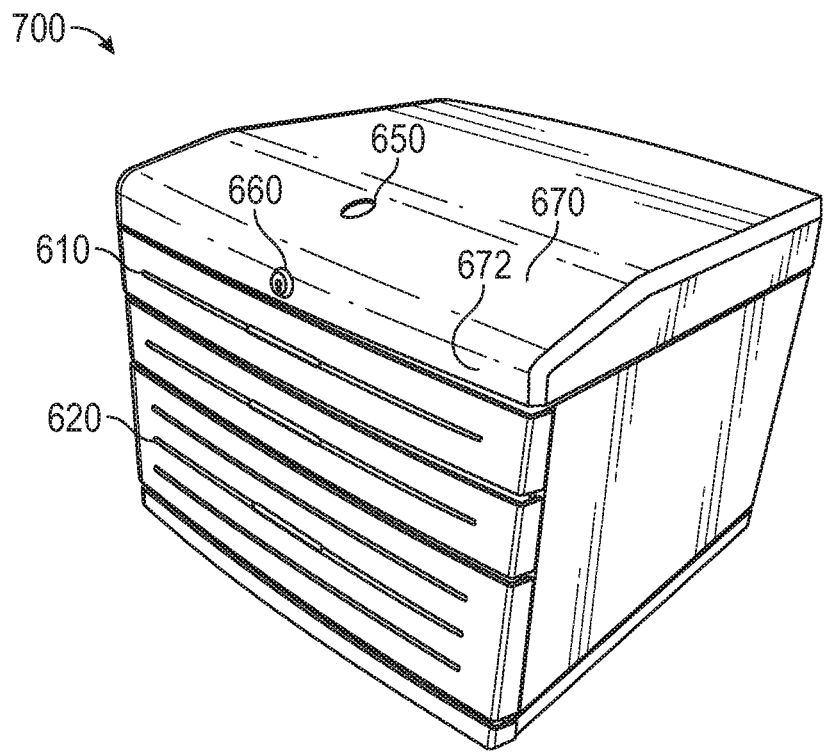
FIG. 7 is a perspective view one or more embodiments of a modular automated dispensing machine.
Figure 8:
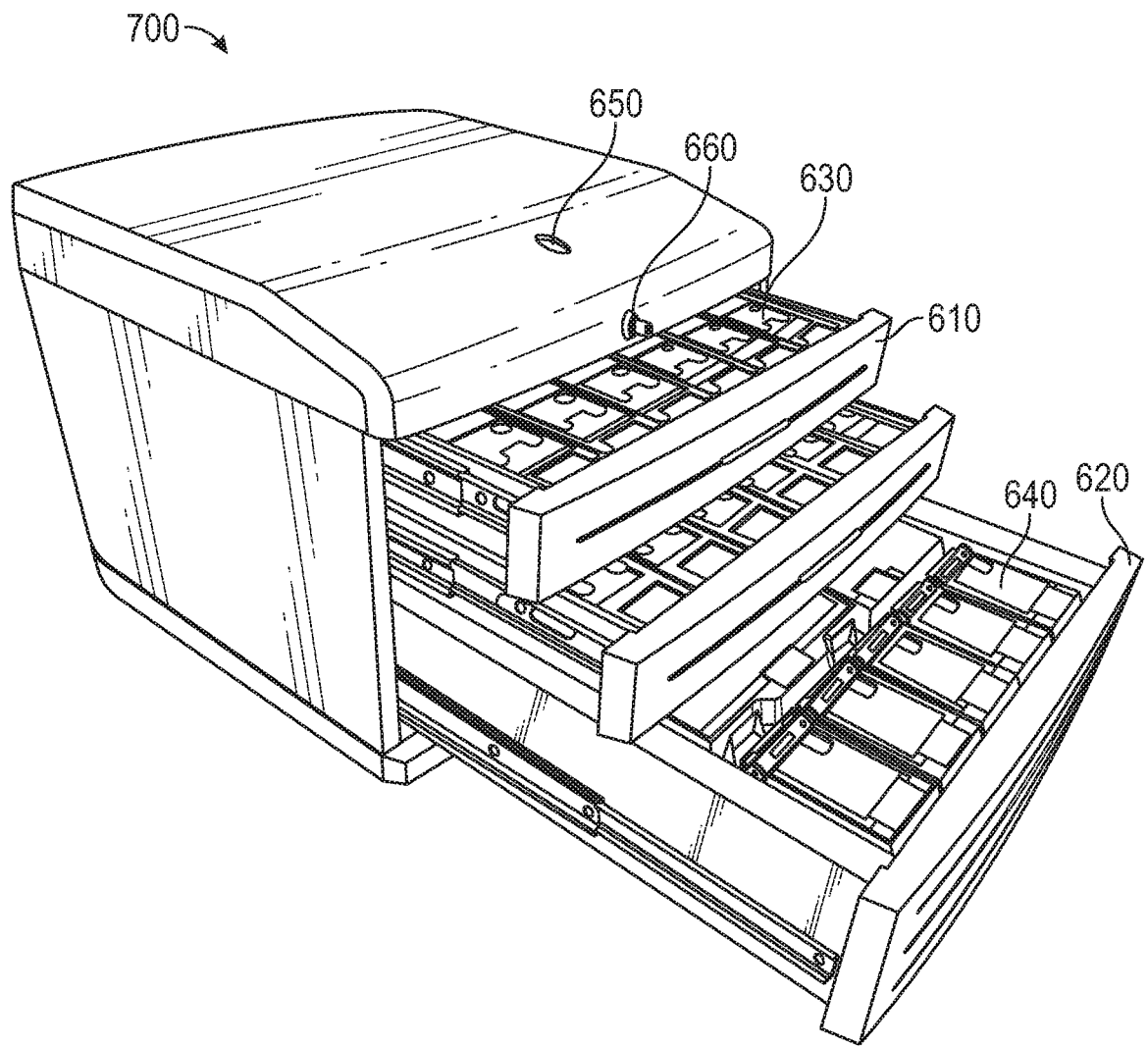
FIG. 8 is a perspective view of the modular automated dispensing machine of FIG. 7 with the drawers in various open positions.
Figure 9:
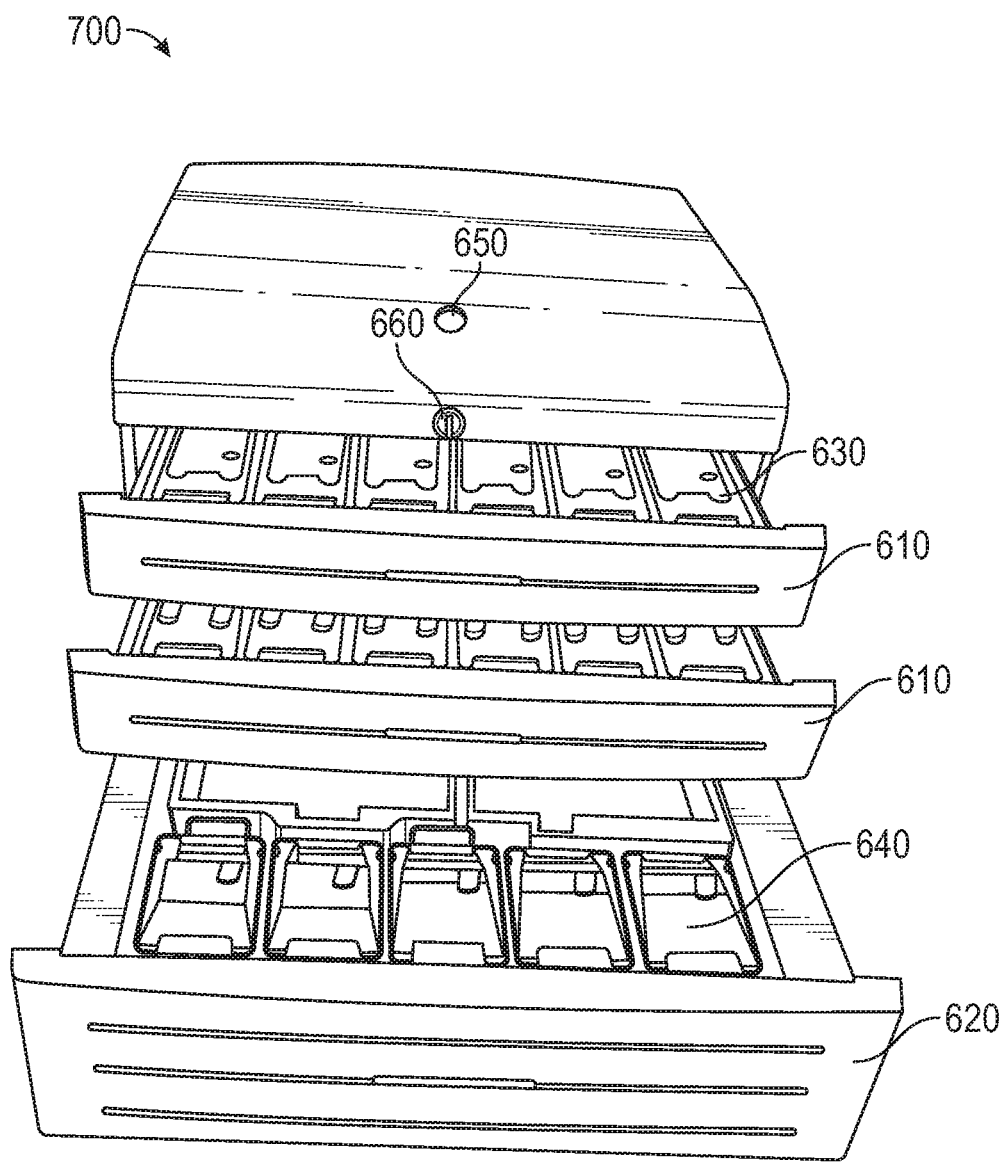
FIG. 9 is a front perspective view of the modular automated dispensing machine of FIG. 7 with the drawers in various open positions.
Figure 10:
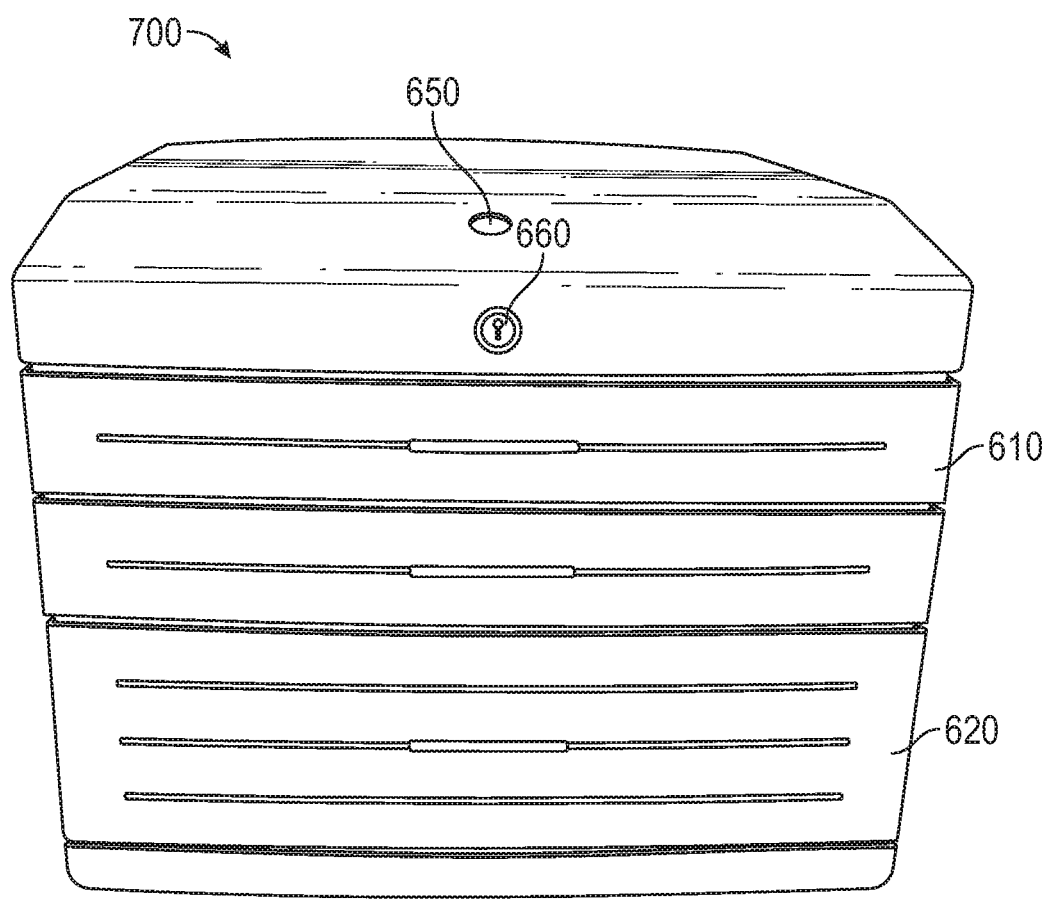
FIG. 10 is a front perspective view of the modular automated dispensing machine of FIG. 7.
Figure 11:
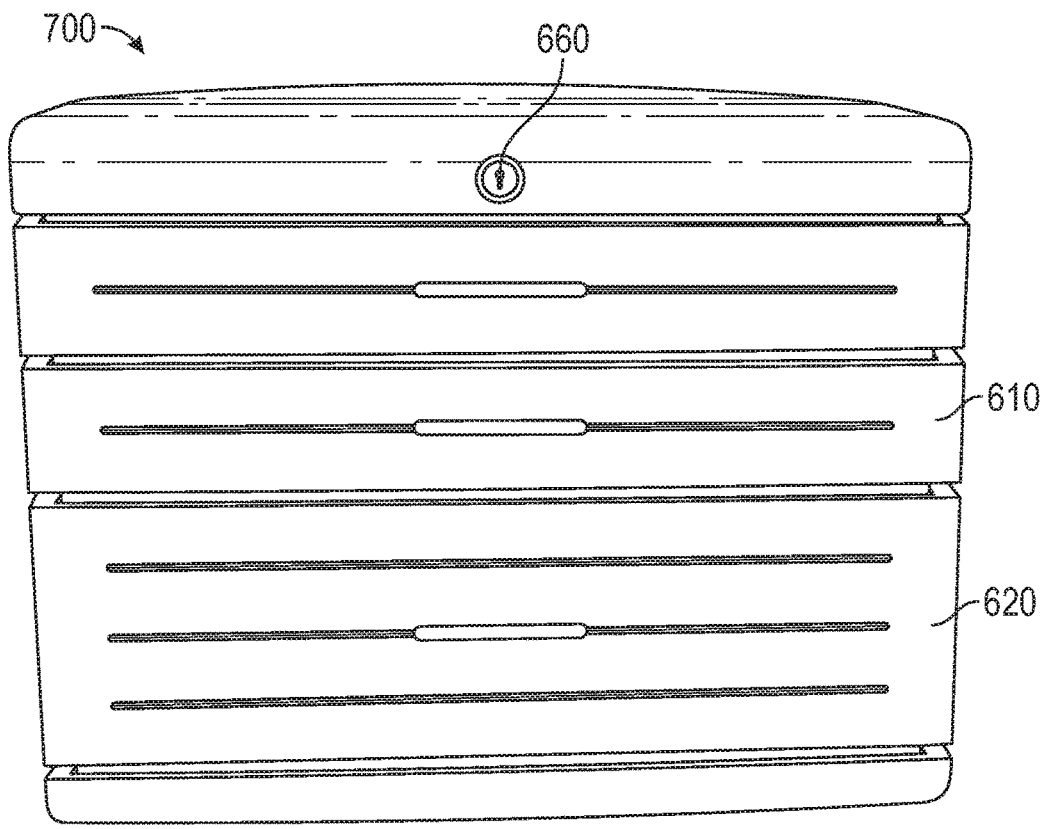
FIG. 11 is a front elevation view of the modular automated dispensing machine of FIG. 7.
Figure 12:
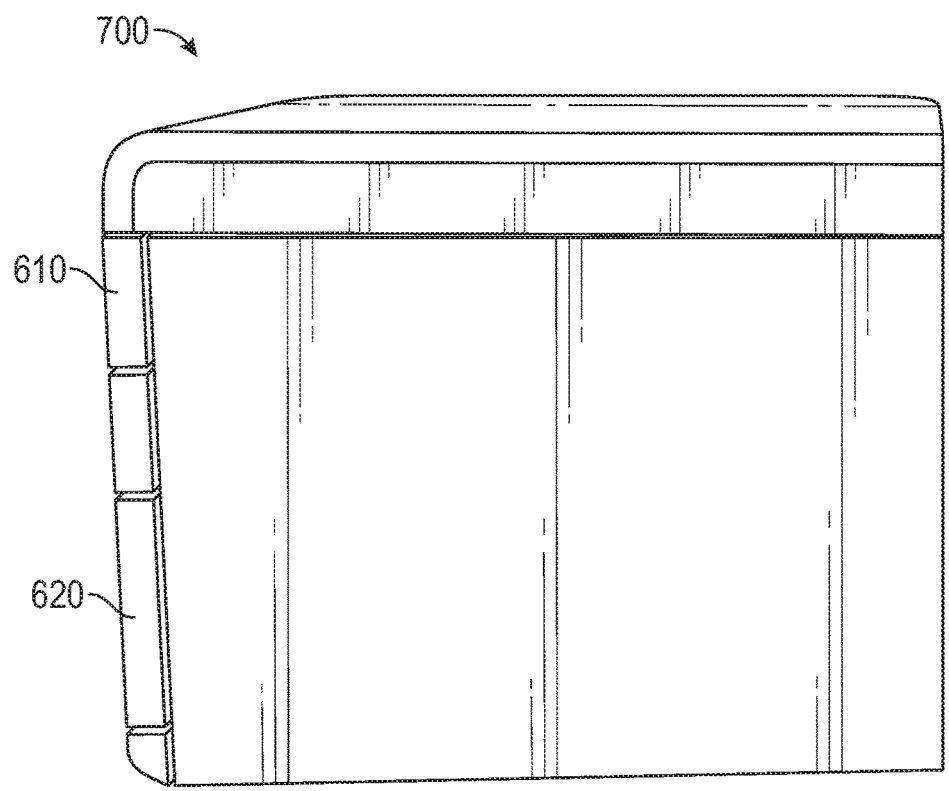
FIG. 12 is a side view of the modular automated dispensing machine of FIG. 7.
Figure 13:
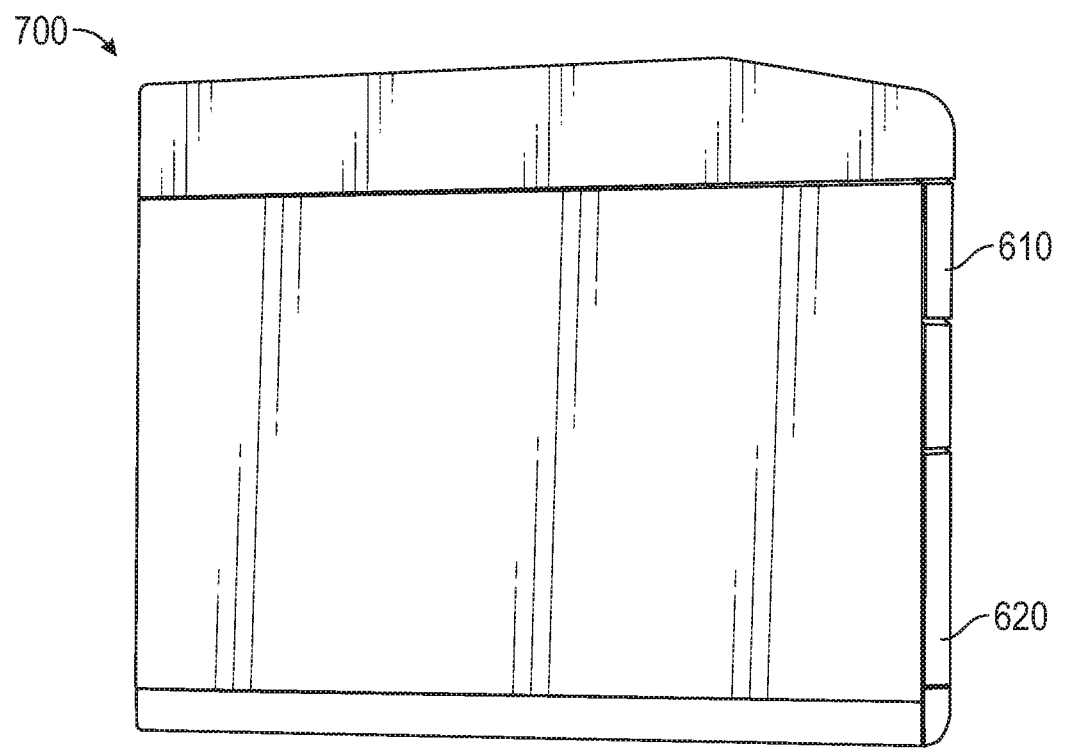
FIG. 13 is another side view of the modular automated dispensing machine of FIG. 7.

As shown in FIGS. 6-17, a MADM is a compact dispensing unit that provides a small footprint. For example, a MADM may be less than 23 inches wide, less than 16 inches high, and 18 inches deep. Accordingly, a MADM may be located in areas that do not require any additional floor space (e.g., a countertop, a shelf, a desk, a cart). A MADM may be configured as a secure enclosure having different numbers and sizes of drawers for storing medications and other materials. For example, a MADM 600 may have four equal sized drawers 610 as shown in FIG. 6. As another example, a MADM 700 may have two equal sized drawers 610 and one larger sized drawer 620 as shown in FIG. 7. The drawers 610, 620 may be configured to only allow one drawer 610, 620 to be open at a time, or to allow all of the drawers 610, 620 to be opened at one time as shown in FIGS. 8 and 9. As also shown in FIGS. 8 and 9, a variety of compartments 630, 640 (e.g., cubes) may be housed in each drawer 610, 620, where each compartment 630, 640 may contain one or more medications or medical devices (e.g., syringes, vials, intravenous (IV) bags). The compartments 630, 640 may be removable such that replenishing the MADM 600, 700 only requires swapping out empty compartments 630, 640 with new pre-loaded compartments 630, 640.

The compartments in each MADM 600, 700 may vary in size, including compartments having uniform size. The disclosed system may be used with compartments of any size. Each compartment may be measured as a space that has a height, width and length. The space creates a volumetric space that will hold a defined quantity of stock for an item. A compartment may be defined as open, secure, or controlled. Each type of compartment may offer a different level of security, control, and tracking of items within the compartment. An open compartment has unrestricted access and may be confined by boundaries (e.g., a bin, dividers, or physical marking). If a user has access to the area (e.g., patient room or other patient care area) where the open compartment is located, the user has access to the open compartment and its items. A secure compartment is confined and controlled through limited access to an item. The secure compartment can be a locking compartment that only contains one dose of one item and a user must have authorization to access the locking compartment. A controlled compartment is one that offers access, with appropriate authorization, to one or many doses of one item. The controlled compartment can be a lidded compartment for which a user must provide appropriate authorization to access the compartment.

Access to a MADM 600, 700 may be secured by one or more forms of access control for authorizing a particular user to open the MADM 600, 700 to retrieve medications. For example, the MADM 600, 700 may include a built in biometric device 650 (e.g., finger print scan, retinal scan, voice recognition). The biometric device 650 may be used for multiple workflow processes, such as user registration, user login and witness authentication. As another example, the MADM 600, 700 may be provided with one or more other forms of access control, such as a key lock, a keypad, an RFID reader, a near field sensor, and the like. As shown in FIGS. 6-8, a fingerprint scanner 650 may be positioned on the top surface 670 of the MADM 600, 700 and a key lock 660 may be positioned on the top front surface 672 of the MADM 600, 700. Here, the key lock 660 may be provided as a backup to the fingerprint scanner 650. For example, the key lock 660 may be used as an override if the power to the MADM 600, 700 is out or the fingerprint scanner 650 is not working.

Figure 14:
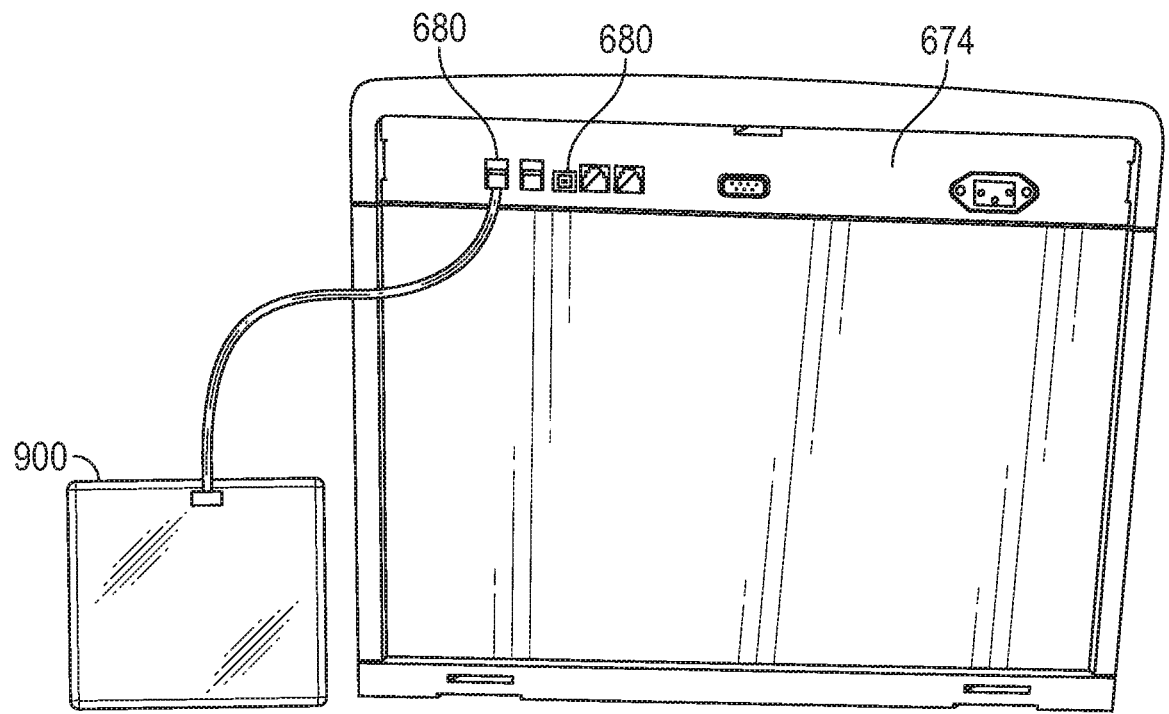
FIG. 14 is a rear view of the modular automated dispensing machine of FIG. 7.
Figure 15:
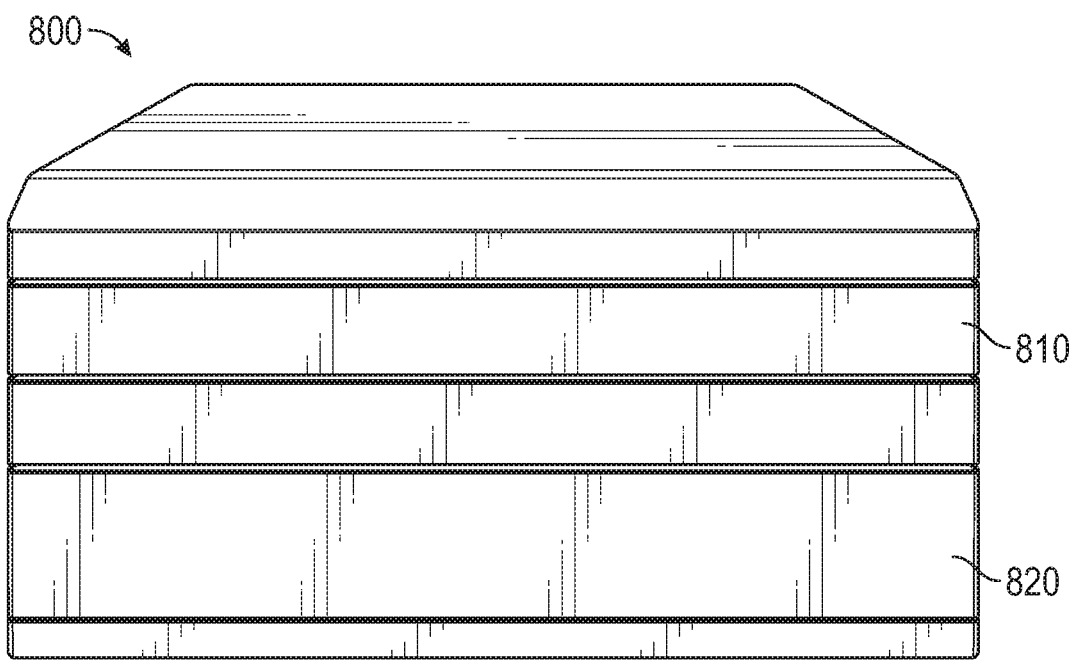
FIG. 15 is a front perspective view of one or more embodiments of a modular automated dispensing machine.
Figure 16:
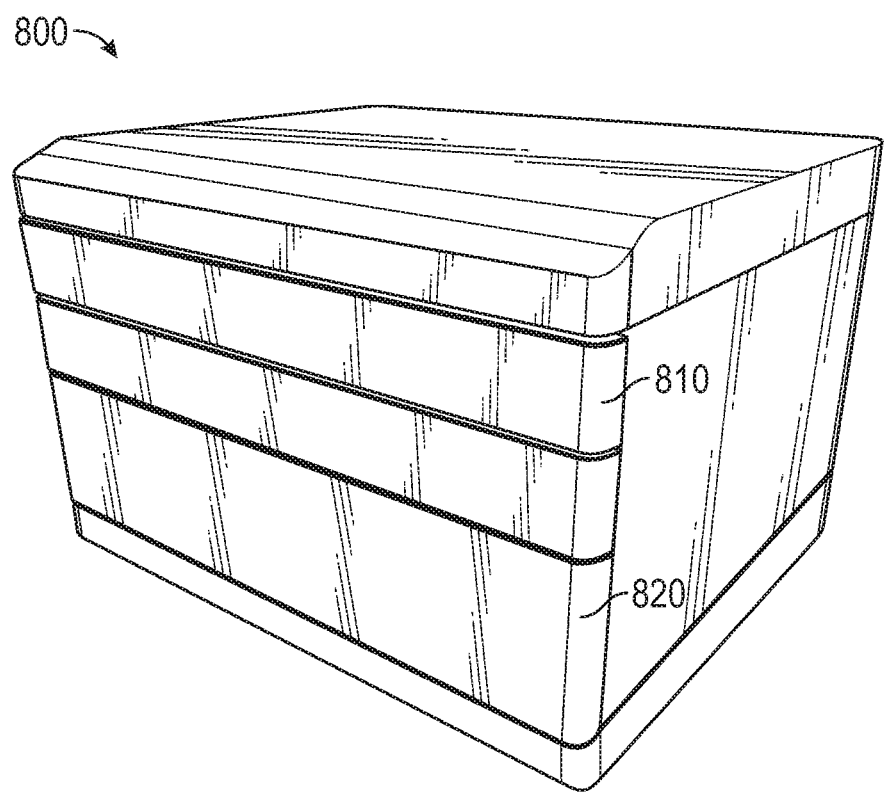
FIG. 16 is a perspective view of the modular automated dispensing machine of FIG. 15.
Figure 17:
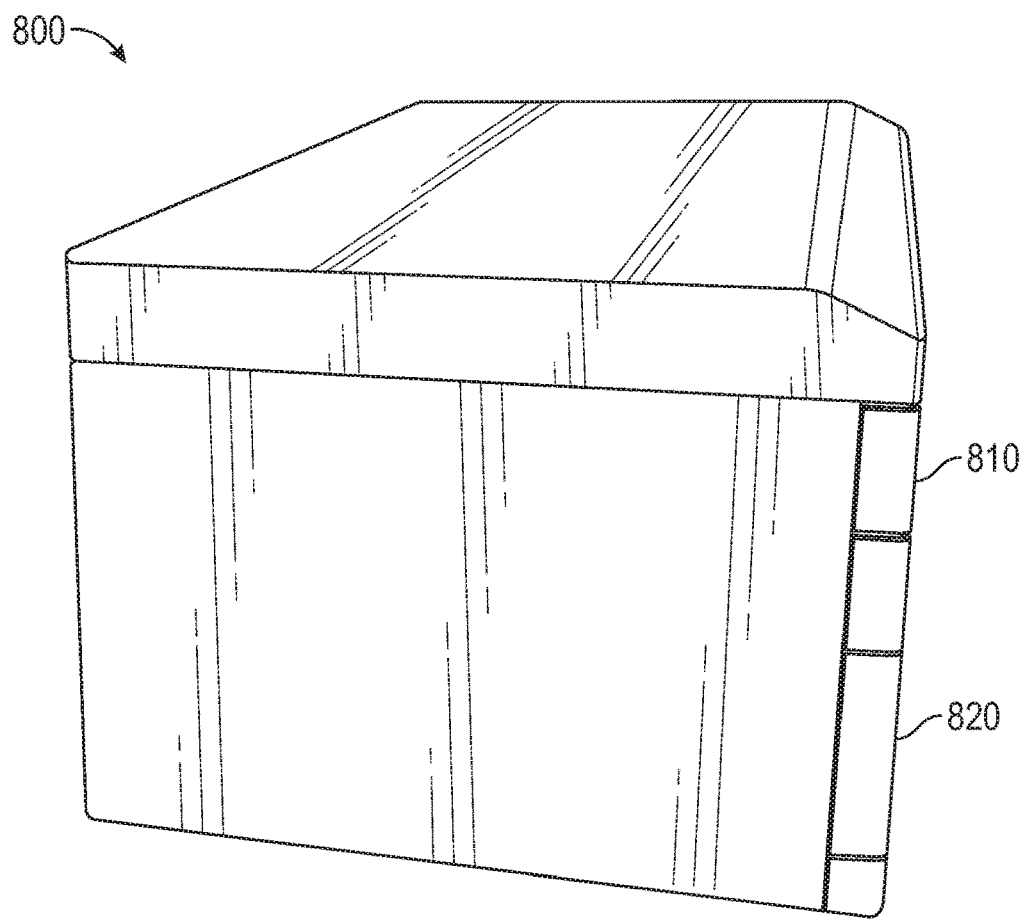
FIG. 17 is a side perspective view of the modular automated dispensing machine of FIG. 15.

As shown in FIGS. 15-17, a MADM 800 may not have any internally built in access control devices or interfaces. Instead, the drawers 810, 820 may be released from a locked state by user authorization provided from an external device (not shown). For example, the MADM 800 may be networked to a cloud based application that allows a user to be authenticated from the user's mobile device (e.g., laptop, tablet, smartphone). As another example, a MADM 600, 700, 800 may have one or more communications ports 680 that provide for the connection of an external access control device 900, as shown in FIG. 14. The example shown in FIG. 14 provides the communications ports 680 positioned or disposed on the back side of the MADM 600, 700, 800. In example aspects, one or more communications ports 680 may be provided on any other suitable area of the MADM 600, 700, 800. For example, the MADM 600, 700, 800 may have the communications ports 680 on the back surface as shown in FIG. 14, as well as an additional communication port 680 positioned on the top front of the MADM 600, 700, 800. The communication ports 680 may be any combination of suitable communications interfaces, such as USB, serial, Ethernet, and the like.

For example, a remote authorization device 900 (e.g., biometric scanner) may be connected to the MADM 600, 700, 800 by a USB port 680. Thus, the user's fingerprint is scanned and authenticated through the remote authorization device 900 to allow access to any MADM 600, 700, 800 that is connected to the remote authorization device 900. Accordingly, one remote authorization device 900 may be used to provide access to multiple MADMs 600, 700, 800. Other suitable peripheral devices may be connected to the communications ports 680. For example, an external scanner (e.g., bar code, RFID) (not shown) may be connected for identification of compartments 630, 640 as they are loaded or refilled. As another example, a printer (not shown) may be connected to provide printing of labels or transaction slips. A networked printer (not shown) may also be used, eliminating the need for connecting a printer to a specific MADM 600, 700, 800. A MADM 600, 700, 800 may also be configured to interface with external peripheral devices through any suitable wireless interface (e.g., WiFi, WLAN, RFID, NFS, Bluetooth).

A MADM 600, 700, 800 may be configured as a new end-point for an existing server based medication dispensing system or application. Here, a MADM 600, 700, 800 may not have an embedded controller. Thus, the server based software may be installed on an existing client computer 950 and the existing client computer 950 is used as the controller to handle the workflow interaction with the MADM 600, 700, 800 (see FIG. 21). Alternatively, the MADM 600, 700, 800 may be networked to access a cloud based server application, where the cloud based server application is used as the controller to handle the workflow interaction with the MADM 600, 700, 800. Thus, a MADM may be a secure storage device with little or no integrated control or authorization devices. As another example, the MADM may have multiple integrated access control devices and an integrated display (e.g. LCD, monitor) (not shown), where the integrated display may provide inventory information.

Figure 18:
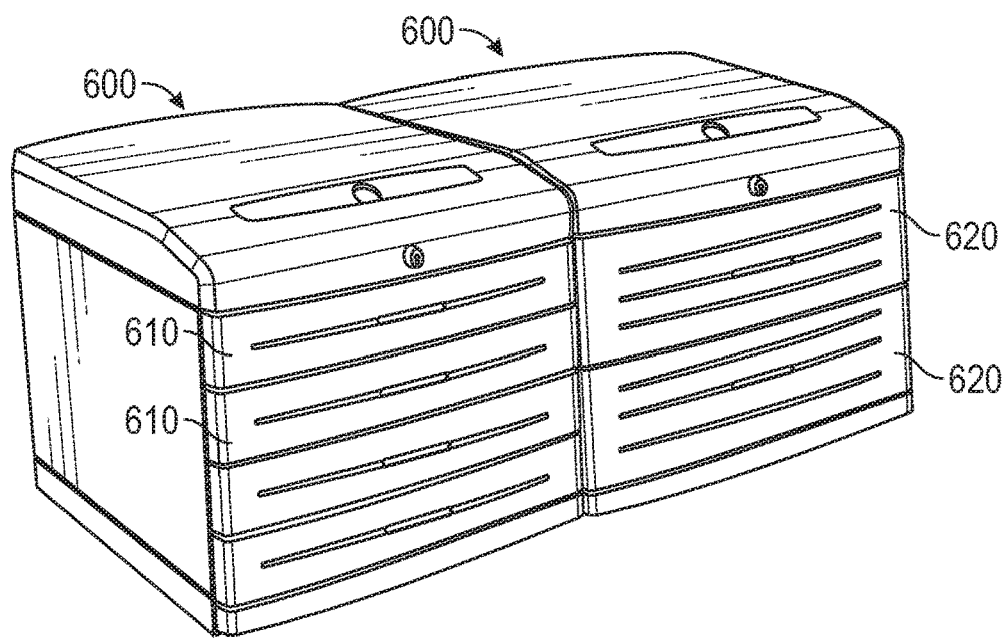
FIG. 18 is a perspective view of two example modular automated dispensing machines connected together.

Multiple MADMs 600, 700, 800 may be connected together for additional flexibility. For example, two MADMs 600 having different drawer 610, 620 configurations may be connected together as shown in FIG. 18. The multiple MADMs 600, 700, 800 may be physically connected to each other or secured individually and positioned next to each other. The multiple MADMs 600, 700, 800 may also be configured as independently functioning units or in a master/slave configuration. As independently functioning units, the multiple MADMs 600, 700, 800 may be connected together or mounted next to each other for space planning or workflow logistic purposes. Here a user interacts with each MADM 600, 700, 800 separately for authorization and access to that particular MADM 600, 700, 800 only. In a master/slave configuration, the MADMs 600, 700, 800 may be interfaced together by a communication cable (e.g., daisy chain) (not shown), and one MADM 600, 700, 800 is configured as the master unit and the other connected MADMs 600, 700, 800 are configured as slave units. Thus, a user may authenticate with just one MADM 600, 700, 800 to gain access to all of the connected MADMs 600, 700, 800.

Figure 19:
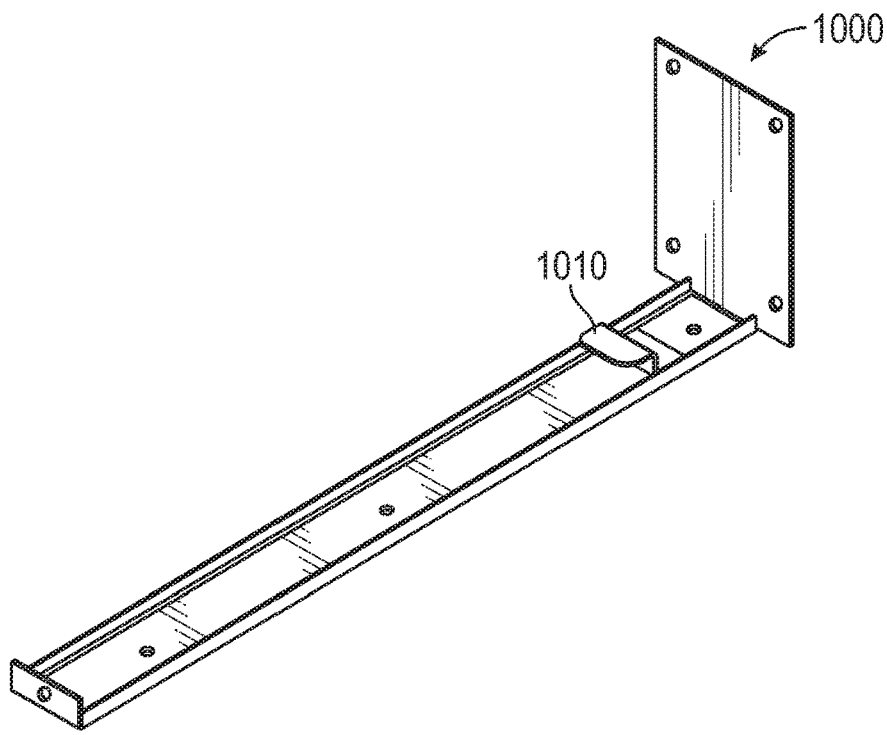
FIG. 19 is a perspective view of one or more embodiments of a mounting device for a modular automated dispensing machine.

A MADM 600, 700, 800 may be configured to be secured to a surface so that the dispensing unit cannot be easily moved, misplaced or stolen. For example, medical rules or building codes may require that medical dispensers be secured against seismic movement, as illustrated by an example bracket 1000 in FIG. 19. The illustrated bracket 1000 may be secured (e.g., bolted, screwed, riveted) to a countertop or table top through the holes on the bottom, secured to wall studs or a vertical surface through the holes on the side, or both. A securing tab 1010 on the bracket 1000 engages with the bottom of the MADM 600, 700, 800. Other mounting devices are also contemplated.

Figure 20:
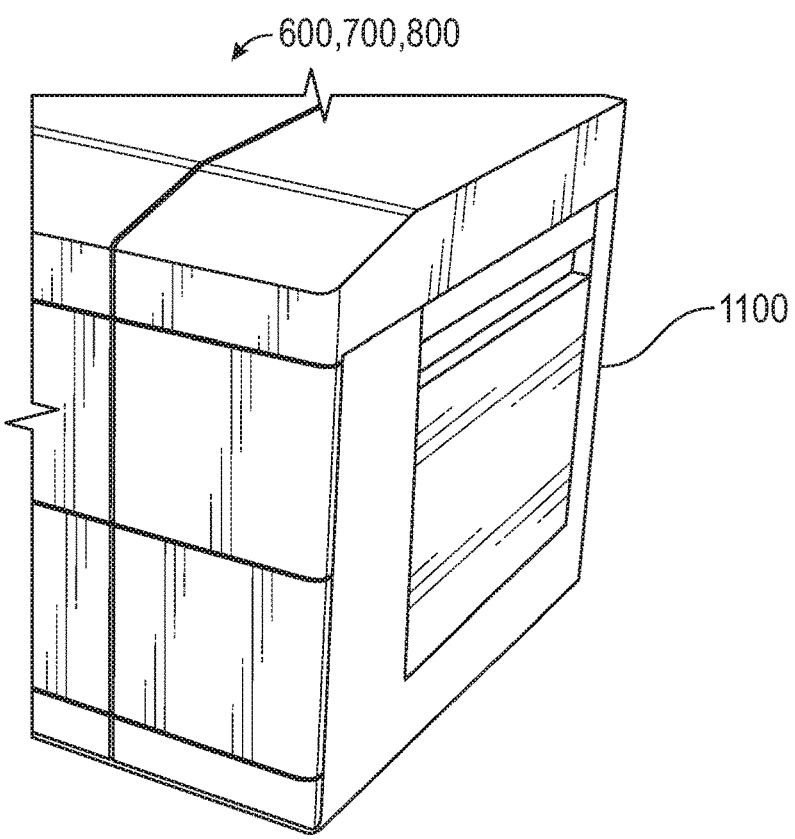
FIG. 20 is a perspective view of one or more embodiments of a return bin for a modular automated dispensing machine.

As shown in FIG. 20, a return bin 1100 may be connected to a MADM 600, 700, 800, allowing for secure return of mistakenly dispensed, unused or waste medications. The returned medication is placed through a slot in the side and is securely held within the return bin 1100. An authorized user may open the return bin 1100 and return, restock or dispose of the returned medication at any time. As another example, a compartment 630, 640 in a drawer of the MADM 600, 700, 800 may be designated as a return compartment. Here, the medication for return may be placed in the return compartment and either the same or other authorized user may later retrieve the contents of the return compartment for restocking, return to another compartment, disposal as waste, and the like.

A MADM 600, 700, 800 may be configured to work with one or more remote management devices (not shown). Here, a remote management device may be a physical device that is mounted to a refrigeration unit or storage cabinet, for example. The remote management device may be configured to monitor the temperature of the refrigerated cabinet, provide alarm or reporting information on variations in the temperature of the refrigerated cabinet, provide access control to the refrigerated cabinet, provide inventor management information regarding medications stored within the refrigerated cabinet, and the like. A MADM 600, 700, 800 may interface with multiple remote management devices, and multiple MADMs 600, 700, 800 may interface to the same remote management device.

Figure 21:
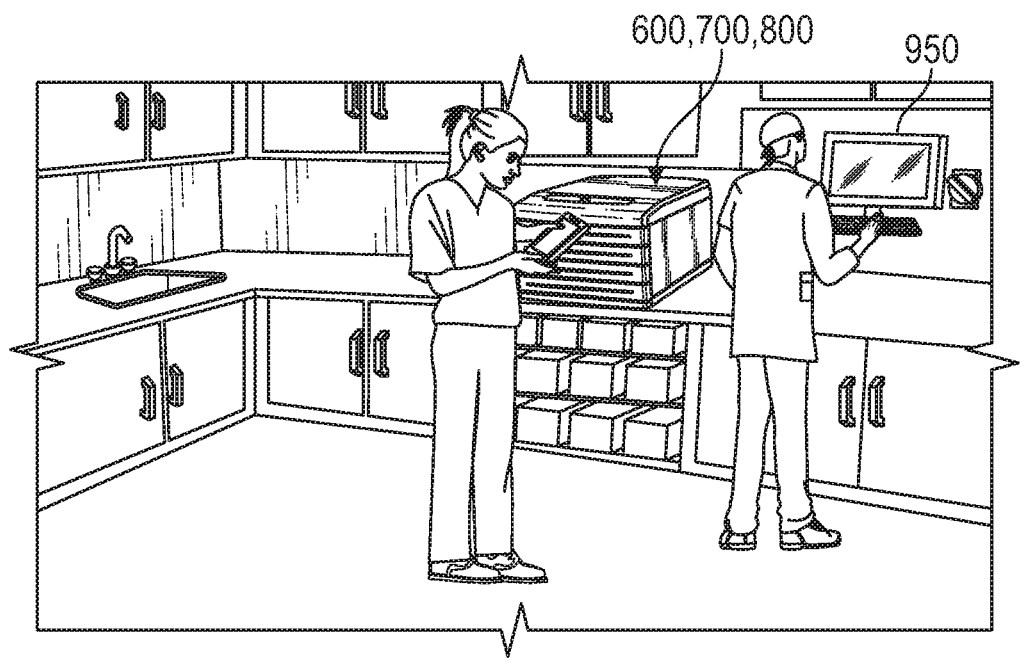
FIG. 21 is an illustration of one or more embodiments of a modular automated dispensing machine in a work environment.

FIG. 21 illustrates an example of a MADM 600, 700, 800 installed in a medical environment. Here the MADM 600, 700, 800 is mounted to a countertop in a common storage area, where authentication is provided through an external computer 950 with a separately mounted monitor and keyboard. Thus, an example workflow process may be that the medical staff person uses the external keyboard and monitor to check medication inventory in the MADM 600, 700, 800 and to queue a specific medication order for dispensing from the MADM 600, 700, 800. The medical staff person may then place a finger on a fingerprint scanner for authentication. Once authenticated, the drawer 610, 620 that contains the queued medication order may release or pop open and the medical staff person then removes the medication and delivers the medication to be administered to a patient or customer.

Another example workflow provides for a user (e.g., doctor, nurse, medical technician) to log into a MADM 600, 700, 800 remotely through the user's mobile device (e.g., laptop, tablet, smartphone). Once logged in, the user may view available inventory in the MADM 600, 700, 800 and/or set up one or more dispensing queues for dispensing medication orders. In one aspect, the user may log in to an enterprise server or application, allowing the user to view inventory and setup dispensing queues in multiple MADMs 600, 700, 800 with just the one log in. In this example, the user may view the inventory in the two MADMs 600 shown in FIG. 18, determining that two medications needed for a particular patient are stored in the first MADM 600 and a third medication needed for the patient is stored in the second MADM 600. The user may then set up dispensing queues in both the first and second MADMs 600. Once the queues are set up, the user may go to the first and second MADMs 600 and authenticate on one or both MADMs 600, depending on whether the MADMs 600 are independently functioning units or in a master/slave configuration. The user then accesses and retrieves the three required medications from the two MADMs 600.

In an example aspect, when the user is at a MADM 600, 700, 800, the system may be configured for the user to view the set up queue of the MADM 600, 700, 800 through the user's mobile device. Alternatively, the MADM 600, 700, 800 may have its own integrated or external display from which the user may view the set up queue without needing to have the user's mobile device present. In this case, the user may interact with the MADM display to select the desired dispensing queue and clear the queue once the medication has been removed from the MADM 600, 700,

800. As another example, the user may view and/or select a dispensing queue from the display and then remove the medication, where an RFID tag on the removed compartment or medication automatically clears the queue and updates the inventory information of the MADM 600, 700, 800.

In one or more embodiments, a MADM 600, 700, 800 may be utilized as the dispensing apparatus 202 to store and dispense optional medications. In one or more embodiments, a MADM 600, 700, 800 may be used to store and dispense required medications. In one or more embodiments, a MADM 600, 700, 800 may be used to store and dispense both required and optional medications.

Figure 22:
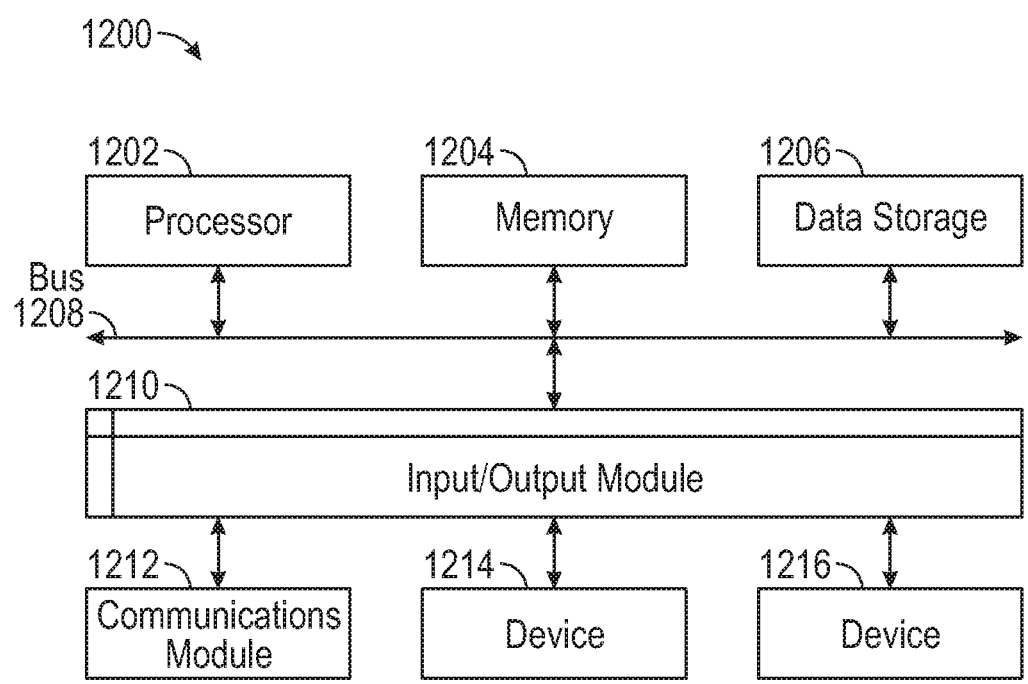
FIG. 22 is a block diagram illustrating an example computer system with which the modular automated dispensing machines of any of FIGS. 2-21 can be implemented.

FIG. 22 is a block diagram illustrating an example computer system 1200 with which the ADM or MADM of FIGS. 2-4 and 6-17 can be implemented. In certain aspects, the computer system 1200 may be implemented using hardware or a combination of software and hardware, either in a dedicated server, or integrated into another entity, or distributed across multiple entities.

Computer system 1200 (e.g., an automated medical dispensing system) includes a bus 1208 or other communication mechanism for communicating information, and a processor 1202 coupled with bus 1208 for processing information. By way of example, the computer system 1200 may be implemented with one or more processors 1202. Processor 1202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 1200 can include, in addition to hardware, code that creates an execution environment for the computer program in question, e.g., code that constitutes processor firmware, a protocol stack, a database management system, an operating system, or a combination of one or more of them stored in an included memory 1204, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1208 for storing information and instructions to be executed by processor 1202. The processor 1202 and the memory 1204 can be supplemented by, or incorporated in, special purpose logic circuitry.

The instructions may be stored in the memory 1204 and implemented in one or more computer program products, i.e., one or more modules of computer program instructions encoded on a computer readable medium for execution by, or to control the operation of, the computer system 1200, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 1204 may also be used for storing temporary variable or other intermediate information during execution of instructions to be executed by processor 1202.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 1200 further includes a data storage device 1206 such as a magnetic disk or optical disk, coupled to bus 1208 for storing information and instructions. Computer system 1200 may be coupled via input/output module 1210 to various devices. The input/output module 1210 can be any input/output module. Example input/output modules 1210 include data ports such as USB ports. The input/output module 1210 is configured to connect to a communications module 1212. Example communications modules 1212 include networking interface cards, such as Ethernet cards and modems. In certain aspects, the input/output module 1210 is configured to connect to a plurality of devices, such as an input device 1214 and/or an output device 1216. Example input devices 1214 include a keyboard and a pointing device, e.g., a mouse or a trackball, by which a user can provide input to the computer system 1200. Other kinds of input devices 1214 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 1216 include display devices, such as a LED (light emitting diode), CRT (cathode ray tube), or LCD (liquid crystal display) screen, for displaying information to the user.

According to one aspect of the present disclosure, the inventory management system can be implemented using a computer system 1200 in response to processor 1202 executing one or more sequences of one or more instructions contained in memory 1204. Such instructions may be read into memory 1204 from another machine-readable medium, such as data storage device 1206. Execution of the sequences of instructions contained in main memory 1204 causes processor 1202 to perform the process steps described herein. One or more processors in a multi-processing arrangement may also be employed to execute the sequences of instructions contained in memory 1204. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the subject matter described in this specification), or any combination of one or more such back end, middleware, or front end components. The components of the system can be interconnected by any form or medium of digital data communication (e.g., a communication network). The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 1200 can include clients and servers. A client and server are generally remote from each other and typically interact through a communication network. The relationship of client and server arises by virtue of computer programs running on the respective computers and having a client-server relationship to each other. Computer system 1200 can be, for example, and without limitation, a desktop computer, laptop computer, or tablet computer. Computer system 1200 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 1202 for execution. Such a medium may take many forms, including, but not limited to, non-volatile media, volatile media, and transmission media. Non-volatile media include, for example, optical disks, magnetic disks, or flash memory, such as data storage device 1206. Volatile media include dynamic memory, such as memory 1204. Transmission media include coaxial cables, copper wire, and fiber optics, including the wires that comprise bus 1208. Common forms of computer-readable media or machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

The invention claimed is:

1. A modular automated dispensing system for dispensing secured medications in a medical environment, the modular automated dispensing system comprising:
   a compact enclosure configured to be disposed on a support surface in a medical treatment area, the compact enclosure comprising a front surface and a top surface;
   a drawer lock assembly;
   one or more drawers for storing medications, each drawer configured to be secured in the compact enclosure when locked by the drawer lock assembly and slideably openable from the front surface of the compact enclosure when unlocked by the drawer lock assembly;
   a plurality of compartments disposed within a respective drawer of the one or more drawers;
   a processor; and
   a biometric input device at least partially disposed within and recessed below the top surface of the compact enclosure such as to receive a biometric signal at the top surface, the biometric input device operatively coupled to the processor and to the drawer lock assembly, the biometric input device configured to provide a first signal to the processor, the first signal comprising one of a registration signal, a login signal and an authentication signal, the processor providing a second signal to the drawer lock assembly based on the first signal, the second signal comprising an unlock signal to unlock the respective drawer, the second signal based on received authorization input from the processor,
   wherein the respective drawer is fully openable to expose all of the plurality of compartments when unlocked by the second signal.

2. The modular automated dispensing system of claim 1, wherein one of the plurality of compartments is configured to be removed and replaced with a similarly sized removable compartment pre-loaded with medications.

3. The modular automated dispensing system of claim 2, further comprising a scanning device configured to scan and enter information associated with the respective compartment upon removing or adding the respective compartment from or to the respective drawer.

4. The modular automated dispensing system of claim 1, wherein the biometric input device comprises one of a fingerprint scanner, a retinal scanner and a voice recognition device.

5. The modular automated dispensing system of claim 4, further comprising a key lock assembly configured to provide access to the compact enclosure if the biometric input device is not operable.

6. The modular automated dispensing system of claim 4, further comprising a key lock assembly, wherein access to the compact enclosure requires successful operation of both the biometric input device and the key lock assembly.

7. The modular automated dispensing system of claim 1, further comprising a network interface configured to unlock the drawer lock assembly upon receiving authentication from a mobile device of an authorized user.

8. The modular automated dispensing system of claim 1, wherein the plurality of compartments comprises a first compartment having no individual compartment lock and a compartment interior that is accessible upon slideably opening the drawer, and a second compartment having an individually lockable compartment lid coupled only to that second compartment and a compartment interior that is not accessible upon initial opening of the respective drawer.

9. The modular automated dispensing system of claim 8, wherein the second compartment is a secure compartment configured to provide access to only a single medication dose upon unlocking the individually lockable compartment lid.

10. The modular automated dispensing system of claim 8, wherein the second compartment is a controlled compartment configured to provide access to a plurality of medication doses upon unlocking the individually lockable compartment lid.

11. The modular automated dispensing system of claim 1, wherein one of the plurality of compartments is a return compartment configured to receive and store previously dispensed medications.

12. The modular automated dispensing system of claim 1, further comprising a remote management device interface, wherein the remote management device interface is configured to communicate with a remote management device on a storage cabinet.

13. The modular automated dispensing system of claim 1, further comprising a mobile device interface configured to provide access to a dispensing queue of the modular automated dispensing system on a display of a mobile device.

14. The modular automated dispensing system of claim 1, further comprising a return bin disposed on an external side surface of the compact enclosure, wherein the return bin includes a bin lock to secure access to contents of the return bin, and wherein the return bin includes a slot disposed on an outer side surface, the slot configured to receive previously dispensed medications when all drawers are closed and secured within the compact enclosure.

15. The modular automated dispensing system of claim 1, further comprising a bracket secured to a top surface of the support surface, the bracket comprising a base disposed parallel to the support surface and a single securing tab projecting upward from the base, the single securing tab configured to engage with a bottom surface of the compact enclosure.

16. A system for dispensing secured medications in a medical environment, the system comprising:
   a plurality of modular automated dispensing devices, each modular dispensing device comprising:
      a compact enclosure configured to be disposed on a support surface above a floor in a medical treatment area, the compact enclosure comprising side surfaces, a rear surface, a front surface, a bottom surface and a top surface;
      a drawer lock assembly;
      one or more drawers for storing medications, each drawer configured to be secured in the compact enclosure when locked by the drawer lock assembly and slideably openable from the front surface of the compact enclosure when unlocked by the drawer lock assembly;
      a plurality of compartments disposed within a respective drawer of the one or more drawers;
      a processor; and
      a biometric input device recessed within the top surface of the compact enclosure such as to receive a biometric signal at the top surface, the biometric input device operatively coupled to the processor, the biometric input device configured to provide a first signal to the processor, the first signal comprising one of a registration signal, a login signal and an authentication signal, the processor providing a second signal to the drawer lock assembly based on the first signal, the second signal comprising an unlock signal to unlock the respective drawer, the second signal based on received authorization input from the processor, wherein the respective drawer is fully openable to expose all of the plurality of compartments when unlocked by the unlock signal.

17. The system of claim 16, further comprising an external access control device operatively connected to one or more of the plurality of modular automated dispensing devices, the external access control device configured to provide user authentication to each of the operatively connected modular automated dispensing devices.

18. The system of claim 17, wherein the external access control device comprises one or more of a fingerprint scanner, a retinal scanner, and a voice recognition device.

19. The system of claim 16, further comprising one or more communication cables connecting the plurality of modular automated dispensing devices, wherein one of the plurality of modular automated dispensing devices is configured as a master device and the remaining modular automated dispensing devices are configured as slave devices.

20. The system of claim 19, wherein the master device is configured to authenticate a user, and wherein any of the plurality of modular automated dispensing devices may be unlocked based on the authentication by the master device.

* * * * *